US010092632B2

(12) United States Patent
Lodge et al.

(10) Patent No.: US 10,092,632 B2
(45) Date of Patent: Oct. 9, 2018

(54) **VACCINATION AGAINST *CRYPTOCOCCUS***

(71) Applicant: Washington University, Saint Louis, MO (US)

(72) Inventors: Jennifer Lodge, Saint Louis, MO (US); Woei Lam, Saint Louis, MO (US); Rajendra Upadhya, Saint Louis, MO (US)

(73) Assignee: Washington University, Saint Louis, MO (US)

(*) Notice: Subject to any disclaimer, the term of this patent is extended or adjusted under 35 U.S.C. 154(b) by 0 days.

(21) Appl. No.: 14/712,567

(22) Filed: May 14, 2015

(65) Prior Publication Data

US 2015/0328295 A1 Nov. 19, 2015

Related U.S. Application Data

(60) Provisional application No. 61/993,964, filed on May 15, 2014.

(51) Int. Cl.
| | |
|---|---|
| *A61K 39/02* | (2006.01) |
| *A61K 39/00* | (2006.01) |
| *A61K 9/00* | (2006.01) |
| *A61K 9/08* | (2006.01) |

(52) U.S. Cl.
CPC ........ *A61K 39/0002* (2013.01); *A61K 9/0043* (2013.01); *A61K 9/0073* (2013.01); *A61K 9/08* (2013.01); *A61K 2039/543* (2013.01); *A61K 2039/544* (2013.01)

(58) Field of Classification Search
None
See application file for complete search history.

(56) References Cited

U.S. PATENT DOCUMENTS

| | | | |
|---|---|---|---|
| 8,460,919 | B2 | 6/2013 | Selitrennikoff |
| 2010/0104604 | A1 | 4/2010 | Selitrennikoff |

OTHER PUBLICATIONS

Baker, L.G., et al.: Chitosan, the deacetylated form of chitin, is necessary for cell wall integrity in Cryptococcus neoformans. Eukaryotic Cell 6: 855-867, 2007.
Baker, L.G., et al.: Cell wall chitosan is necessary for virulence in the opportunistic pathogen Cryptococcus neoformans. Eukaryotic Cell 10: 1264-1268, 2011.
Banks, I.R., et al.: A chitin synthase and its regulator protein are critical for chitosan production and growth of the fungal pathogen *Cryptococcus neoformans*. Eukaryotic Cell 4: 1902-1912, 2005.
Datta, K., and Pirofski, L., Towards a vaccine for Cryptococcus neoformans: principles and caveats. FEMS Yeast Res. 6: 525-536, 2006.
De Jesus, M. et al. Glucuronoxylomannan, galactoxylomannan and mannoprotein occupy spatially separate and discrete regions in the capsule of Cryptococcus neoformans. Virulence 1:6, 500-508 (Nov./Dec. 2010).
Fuchs, B.B., et al.. Susceptibility of Cryptococcus neoformans to photodynamic inactivation is associated with cell wall integrity. Antimicrobial Agents and Chemotherapy 51: 2929-2936, 2007.
Hole, CR and Wormley FL Vaccine and immunotherapeutic approaches for the prevention of cryptococcosis: lessons learned from animal models. Frontiers in Microbiology vol. 3 Article 291 doi: 10.3389/fmicb.2012.00291 (Aug. 2012).
Levitz et al. Molecular characterization of a mannoprotein with homology to chitin deacetylases that stimulates T cell responses to Cryptococcus neoformans. PNAS 98:18 10422-10427 (Aug. 2001).
Lockhart, S.R., et al. Cryptococcus gattii in the United States: genotypic diversity of human and veterinary isolates. PLOS One 8: issue 9 e74737, 2013.
Rodrigues, G.B., et al.: In vitro photodynamic inactivation of Cryptococcus neoformans melanized cells with chloroaluminum phthalocyanine nanoemulsion. Photochemistry and Photobiology 88: 440-447, 2012.
Wormley, FL et al. Protection against Cryptococcosis by Using a Murine Gamma Interferon-Producing Cryptococcus neoformans Strain. Infection and Immunity 75:3, 1453-1462 (Mar. 2007).
Wüthrich, M. et al. Safety, Tolerability, and Immunogenicity of a Recombinant, Genetically Engineered, Live-Attenuated Vaccine against Canine Blastomycosis. Clinical and Vaccine Immunology 18:5, 783-789 (May 2011).

*Primary Examiner* — Jennifer E Graser
(74) *Attorney, Agent, or Firm* — Zackson Law LLC; Saul L. Zackson

(57) ABSTRACT

Vaccines and methods of inoculation for conferring immunity to *Cryptococcus* infection are disclosed. Strains of *Cryptococcus* fungi, including *Cryptococcus neoformans* and *Cryptococcus gattii*, can be administered to a human or animal subject via inhalation. *Cryptococcus* fungi that can be used to confer immunity can comprise one or more mutations in genes that contribute to chitosan production, such as genes encoding a chitin deacetylase (cda), a chitin synthase (chs) and/or a regulator of chitin synthase (csr). Inhalation administration of heat-killed *Cryptococcus* harboring deletions in cda1, cda2 and cda3 genes can confer immunity. In a murine model system, inhalation administration of *Cryptococcus neoformans* harboring deletions in cda1, cda2 and cda3 genes conferred immunity against subsequent exposure to wild type *Cryptococcus neoformans* in 100% of test animals. Inhalation administration of heat-killed *Cryptococcus* grown under conditions leading to reduced chitosan production can also confer immunity.

6 Claims, 11 Drawing Sheets

Specification includes a Sequence Listing.

VACCINATION AGAINST *CRYPTOCOCCUS*

PRIORITY

This application claims the benefit of U.S. Provisional Application No. 61/933,964, filed on May 15, 2014, which is hereby incorporated by reference in its entirety.

STATEMENT OF GOVERNMENT SUPPORT

This it was made with government support under AI072195 awarded by the National Institutes of Health. The government has certain rights in the invention.

REFERENCE TO A SEQUENCE LISTING

The Sequence Listing, which is a part of the present disclosure, includes a text file comprising primer nucleotide and/or amino acid sequences of the present invention. The subject matter of the Sequence Listing is incorporated herein by reference in its entirety. The information recorded in computer readable form is identical to the written sequence listing.

Introduction

*Cryptococcus* fungi, such as *Cryptococcus neoformans* and *Cryptococcus gattii* are pathogenic fungi that are found world-wide. *Cryptococcus neoformans* causes meningoencephalitis, particularly in immunocompromised individuals. It is invariably fatal unless treated, and the current antifungals are inadequate to effectively cure this disease, due to inherent toxicities or the inability to kill the fungus and prevent relapse. Recent studies have indicated that there are over 1,000,000 new cases of cryptococcosis in the world each year, which results in over 600,000 deaths. *Cryptococcus neoformans* is known to appear as an opportunistic infection in AIDS patients.

The fungus *Cryptococcus gattii* also infects humans, and can cause pulmonary diseases such as pulmonary cryptococcosis, basal meningitis, and cerebral cryptococcomas. *Cryptococcus gattii* has also been associated with infections of skin, soft tissue, lymph node, bone, and joints. *Cryptococcus gattii* is also known to infect non-human mammals, such as dogs, cats, camelids, horses, sheep, goats, cows, koalas and dolphins (Lockhart, S. R., et al., *PLOS ONE* 8: issue 9 e74737, 2013).

Banks, I. R., et al., *Eukaryotic Cell* 4: 1902-1912, 2005 discloses that a chitin synthase (CHS3) and its regulator protein (CSR2) are critical for chitosan production and growth in *Cryptococcus neoformans*. These authors show that deletions chs3Δ and csr2Δ are defective in chitosan production. Although this reference suggests that chitin synthesis could serve as an antifungal target, it does not teach nor suggest the use of the disclosed strains for vaccines against *Cryptococcus* infection.

Baker, L. G., et al., *Eukaryotic Cell* 6: 855-867, 2007 discloses that chitosan, a deacetylated form of chitin, is necessary for cell wall integrity in *Cryptococcus neoformans*. These workers demonstrated that three deacetylases, Cda1, Cda2 and Cda3 can account for all chitosan produced during vegetative growth of *Cryptococcus neoformans* in culture. Several deletions of chitin deacetylases genes, including cda1Δ, cda2Δ, cda3Δ, cda1Δcda2Δ, cda1Δcda3Δ, cda2Δcda3Δ and cda1Δcda2Δcda3Δ were described. However, none of these strains are described as conferring immunity against *Cryptococcus neoformans* infection.

Baker, L. G., et al., *Eukaryotic Cell* 10: 1264-1268, 2011 discloses that *Cryptococcus neoformans* strains deleted for chitin deacetylases genes exhibit less virulence in mice. These authors show in a model system that intranasal inoculation of mice with wild type *Cryptococcus neoformans* reduced survival to 0% by 19 days, whereas intranasal inoculation with *Cryptococcus neoformans* having one or more genetic deletions in chitin deacetylase(s) did not lead to loss of survival over a 60 day period. However, the reference did not describe any vaccine against *Cryptococcus* infection or methods of conferring immunity against *Cryptococcus* infection.

There is no effective vaccine against *Cryptococcus neoformans* or *Cryptococcus gattii* (Datta, K., and Pirofski, L., *FEMS Yeast Res.* 6: 525-536, 2006). Compositions and methods for preventing *Cryptococcus neoformans* and *Cryptococcus gattii* infection are needed.

SUMMARY

The inventors have developed vaccines effective in humans and animals against infection by *Cryptococcus* fungi, including *Cryptococcus neoformans* and *Cryptococcus gattii*. The inventors have also developed novel methods of administration of vaccine formulations.

In some embodiments, the present teachings include a vaccine against a *Cryptococcus* fungus such as *C. neoformans* or *C. gattii* which can be effective for protecting humans and various non-human animals against a *Cryptococcus* infection such as *Cryptococcus neoformans* infection and/or *Cryptococcus gattii* infection. In various aspects, a method of the present teachings can comprise administering to the lungs of a subject a *Cryptococcus* fungus deficient for chitosan. In some configurations, the *Cryptococcus* fungus can be a wild type *Cryptococcus* fungus deficient for chitosan that can comprise, consist of, or consist essentially of no more than 60%, 55%, 50%, 45%, 40%, 35%, 30%, 25%, 20%, 15%, 10%, 9%, 8%, 7%, 6%, 5%, 4%, 3%, 2%, or 1% of the chitosan level compared to a wild type *Cryptococcus* grown on yeast extract peptone dextrose (YPD). In some configurations, the *Cryptococcus* fungus deficient for chitosan can be a *Cryptococcus* fungus grown in yeast nitrogen base (YNB) medium. In some configurations, the medium can be buffered to pH 7.0 with a buffering agent such as, without limitation 3-(N-morpholino)propanesulfonic acid (MOPS).

In some configurations, the *Cryptococcus* fungus deficient for chitosan can be a *Cryptococcus neoformans* fungus deficient for chitosan or a *Cryptococcus gattii* fungus deficient for chitosan. In some configurations, the *Cryptococcus* fungus deficient for chitosan can be a viable *Cryptococcus* fungus deficient for chitosan or an inactivated *Cryptococcus* fungus deficient for chitosan. In some configurations, the *Cryptococcus* fungus deficient for chitosan can be a *Cryptococcus* fungus deleted for at least one, at least two, at least three chitin deacetylase genes such as, without limitation, cda1Δ, cda2Δ and cda3Δ or a combination thereof. In various configurations, the *Cryptococcus* fungus deficient for chitosan can be a *Cryptococcus* fungus deleted for at least a chitin synthase (chs) gene such as, without limitation, chs3Δ. In some configurations, the *Cryptococcus* fungus deficient for chitosan can be a *Cryptococcus* fungus deleted for at least one chitin synthase regulator (csr) gene, such as, without limitation csr2Δ. In some configurations, the *Cryptococcus* fungus deficient for chitosan production can comprise, consist of, or consist essentially of a deletion or an inactivating mutation in at least one, at least two, at least three, or at least 4 gene(s) selected from the group consisting of cda1, cda2, cda3, chs3 and csr2 or a combination thereof.

In some configuration, the administering by inhalation to the lungs can comprise nasal inhalation, oral inhalation, or a combination thereof. In some configurations, the nasal inhalation can be selected from the group consisting of inhaling a nose drop formulation and inhaling a nasal spray formulation.

In some embodiments, a vaccine of the present teachings can include a *Cryptococcus neoformans* strain deficient for chitosan production. In some embodiments, the *Cryptococcus neoformans* deficient for chitosan production can be inactivated. In some embodiments, the *Cryptococcus neoformans* deficient for chitosan production can be viable. In some embodiments, a vaccine of the present teachings can include a *Cryptococcus neoformans* strain blocked for chitosan production. In various aspects, a vaccine of the present teachings can include a *Cryptococcus neoformans* strain deficient for chitosan.

In various configurations, a *Cryptococcus* strain of the present teachings can comprise less than 20% of wild-type level of chitosan, less than 15% of wild-type level of chitosan, less than 10% of wild-type level of chitosan, less than 5% of wild-type level of chitosan, less than 1% of wild-type level of chitosan, or less than 0.1% of level of chitosan compared to its wild-type parent strain. In various configurations, a *Cryptococcus* strain of the present teachings can comprise no chitosan.

In various configurations, a *Cryptococcus neoformans* strain deficient for chitosan production can have one or more genetic mutations in gene(s) encoding chitin deacetylase (cda). In some aspects, the one or more genetic mutations can reduce or eliminate the ability of the fungus to produce chitosan. In some aspects, a genetic mutation can be a deletion. In various configurations, a *Cryptococcus neoformans* strain deficient for chitosan production can have one or more genetic lesions of one or more cda genes. A genetic lesion of the present teachings can include a deletion mutation, a point mutation, an insertion mutation, and/or a frameshift mutation of any cda gene, such as, for example and without limitation, a cda1 gene, a cda2 gene, and/or a cda3 gene, or any combination thereof. In various configurations, a genetic mutation can reduce or eliminate expression of a functional cda gene product. In some configurations, a genetic deletion can reduce or eliminate expression of a cda gene. In various configurations, a *Cryptococcus neoformans* strain of the present teachings can have deletions and/or inactivating mutations in the cda1 gene, the cda2 gene, the cda 3 gene, a combination of mutations in the cda1 and cda2 genes, the cda1 and cda3 genes, the cda2 and cda3 genes, or the cda1, cda2 and cda3 genes.

In various configurations, a *Cryptococcus* strain deficient for chitosan production that can be used in a vaccine can be a viable *Cryptococcus* strain deficient for chitosan production, or an inactivated *Cryptococcus* strain deficient for chitosan production. In some configurations, an inactivated *Cryptococcus* strain deficient for chitosan production can comprise heat-killed or heat-attenuated *Cryptococcus* deficient for chitosan production. In some configurations, an inactivated *Cryptococcus* strain deficient for chitosan production can comprise *Cryptococcus* deficient for chitosan production that had been killed by exposure to electromagnetic radiation such as ultraviolet light, gamma ray radiation, or x-ray radiation, by exposure to nuclear radiation such as exposure to an alpha particle emitting source or a beta particle emitting source, by exposure to a toxic chemical, or by photodynamic inactivation (Rodrigues, G. B., et al., *Photochemistry and Photobiology* 88:440-447, 2012; Fuchs, B. B., et al., *Antimicrobial Agents and Chemotherapy* 51:2929-2936, 2007).

In various configurations, a *Cryptococcus neoformans* strain deficient for chitosan production that can be used in a vaccine can be a viable *Cryptococcus neoformans* strain deficient for chitosan production, or an inactivated *Cryptococcus neoformans* strain deficient for chitosan production. In some configurations, an inactivated *Cryptococcus neoformans* strain deficient for chitosan production can comprise heat-killed or heat-attenuated *Cryptococcus neoformans* deficient for chitosan production. In some configurations, an inactivated *Cryptococcus neoformans* deficient for chitosan production can comprise *Cryptococcus neoformans* deficient for chitosan production that had been killed by exposure to electromagnetic radiation such as ultraviolet light, gamma ray radiation, or x-ray radiation, by exposure to nuclear radiation such as exposure to an alpha particle emitting source or a beta particle emitting source, by exposure to a toxic chemical, or by photodynamic inactivation (Rodrigues, G. B., et al., Photochemistry and Photobiology 88:440-447, 2012; Fuchs, B. B., et al., Antimicrobial Agents and Chemotherapy 51: 2929-2936, 2007).

In various configurations, a *Cryptococcus gattii* strain deficient for chitosan production that can be used in a vaccine can be a viable *Cryptococcus gattii* strain deficient for chitosan production, or an inactivated *Cryptococcus gattii* strain deficient for chitosan production. In some configurations, an inactivated *Cryptococcus gattii* strain deficient for chitosan production can comprise heat-killed or heat-attenuated *Cryptococcus gattii* deficient for chitosan production. In some configurations, an inactivated *Cryptococcus gattii* deficient for chitosan production can comprise *Cryptococcus gattii* deficient for chitosan production that had been killed by exposure to electromagnetic radiation such as ultraviolet light, gamma ray radiation, or x-ray radiation, by exposure to nuclear radiation such as exposure to an alpha particle emitting source or a beta particle emitting source, by exposure to a toxic chemical, or by photodynamic inactivation (Rodrigues, G. B., et al., *Photochemistry and Photobiology* 88: 440-447, 2012; Fuchs, B. B., et al., *Antimicrobial Agents and Chemotherapy* 51:2929-2936, 2007).

In various embodiments, methods are disclosed of conferring immunity against *Cryptococcus* infection. In various configurations, these methods include pulmonary administration of an immune response-inducing amount of a *Cryptococcus* strain deficient for chitosan production. In various configurations, these methods include nasal administration of a *Cryptococcus* strain deficient for chitosan production. In various configurations, a *Cryptococcus* strain deficient for chitosan production can be administered to the lungs of a subject by inhalation of the *Cryptococcus* via the nose, mouth or a combination thereof. In various configurations, administration of a *Cryptococcus* strain deficient for chitosan production for inhalation can be accomplished using pharmaceutically acceptable means, such as, without limitation, nose drops or nasal spray. In some configurations, a *Cryptococcus* strain deficient for chitosan production which can be used for inhalation administration can be a live strain of *Cryptococcus* deficient for chitosan production. In some configurations, a *Cryptococcus* strain deficient for chitosan production which can be used for inhalation administration can be an inactivated strain of *Cryptococcus* deficient for chitosan production.

In various embodiments, the inventors disclose methods of conferring immunity against *Cryptococcus neoformans* infection. In various configurations, these methods include pulmonary administration of an immune response-inducing amount of a *Cryptococcus neoformans* strain deficient for chitosan production. In various configurations, these methods include pulmonary administration, which can be via nasal inhalation and/or oral inhalation, of a *Cryptococcus neoformans* strain deficient for chitosan production. In various configurations, a *Cryptococcus* neoformans strain deficient for chitosan production can be administered to the lungs of a subject via inhalation of the *Cryptococcus neoformans* via the nose and/or mouth. In various configurations, administration of a *Cryptococcus neoformans* strain deficient for chitosan production for inhalation can be accomplished using pharmaceutically acceptable compositions, such as, without limitation, nose drops or nasal spray. In some configurations, a *Cryptococcus neoformans* strain deficient for chitosan production which can be used for inhalation administration can be a live strain of *Cryptococcus neoformans* deficient for chitosan production. In some configurations, a *Cryptococcus* strain deficient for chitosan production which can be used for inhalation administration can be an inactivated strain of *Cryptococcus neoformans* deficient for chitosan production.

In various embodiments, methods are disclosed of conferring immunity against *Cryptococcus gattii* infection. In various configurations, these methods can include pulmonary administration of an immune response-inducing amount of a *Cryptococcus gattii* strain deficient for chitosan production. In various configurations, these methods include nasal administration of a *Cryptococcus gattii* strain deficient for chitosan production. In various configurations, a *Cryptococcus gattii* strain deficient for chitosan production can be administered to the lungs of a subject via inhalation of the *Cryptococcus gattii* via the nose or mouth. In various configurations, administration of a *Cryptococcus gattii* strain deficient for chitosan production for inhalation can be accomplished using pharmaceutically acceptable means, such as, without limitation, nose drops or nasal spray. In various configurations, administration of a *Cryptococcus gattii* strain deficient for chitosan production for inhalation can be accomplished using pharmaceutically acceptable means, such as, without limitation, nose drops or nasal spray. In some configurations, a *Cryptococcus gattii* strain deficient for chitosan production which can be used for inhalation administration can be a live strain of *Cryptococcus gattii* deficient for chitosan production. In some configurations, a *Cryptococcus* strain deficient for chitosan production which can be used for inhalation administration can be an inactivated strain of *Cryptococcus gattii* deficient for chitosan production.

In various embodiments, the inventors disclose methods of conferring immunity against *Cryptococcus gattii* infection. In various configurations, these methods include pulmonary administration of an immune response-inducing amount of a *Cryptococcus neoformans* strain deficient for chitosan production. In various configurations, these methods include nasal administration of a *Cryptococcus neoformans* strain deficient for chitosan production. In various configurations, a *Cryptococcus neoformans* strain deficient for chitosan production can be administered to the lungs of a subject via inhalation of the *Cryptococcus neoformans* via the nose or mouth. In various configurations, administration of a *Cryptococcus neoformans* strain deficient for chitosan production for inhalation can be accomplished using pharmaceutically acceptable means, such as, without limitation, nose drops or nasal spray.

In various embodiments, a subject that can be vaccinated against a *Cryptococcus* such as *Cryptococcus neoformans* or *Cryptococcus gattii* can be a human. In various embodiments, a subject that can be vaccinated against *Cryptococcus neoformans* or *Cryptococcus gattii* can be a non-human mammal, such as, without limitation, a dog, a cat, a camelid such as an alpaca or a llama, a rodent such as a laboratory mouse, or a farm animal such as an equine, a bovine, a caprine or an ovine.

In some embodiments, the present teachings include a vaccine against *Cryptococcus gattii* which can be effective for protecting humans and various non-human animals against *Cryptococcus gattii* infection. In various aspects, a vaccine of the present teachings can include a *Cryptococcus gattii* strain deficient for chitosan production. In some embodiments, the *Cryptococcus gattii* deficient for chitosan production can be inactivated. In some embodiments, the *Cryptococcus gattii* deficient for chitosan production can be viable. In some embodiments, a vaccine of the present teachings can include a *Cryptococcus gattii* strain blocked for chitosan production. In various aspects, a vaccine of the present teachings can include a *Cryptococcus gattii* strain deficient for chitosan.

In some embodiments, the present teachings include a vaccine against *Cryptococcus gattii* which can be effective for protecting humans and various non-human animals against *Cryptococcus gattii* infection. In various aspects, a vaccine of the present teachings can include a *Cryptococcus neoformans* strain deficient for chitosan production. In some embodiments, the *Cryptococcus neoformans* deficient for chitosan production can be inactivated. In some embodiments, the *Cryptococcus neoformans* deficient for chitosan production can be viable. In some embodiments, a vaccine of the present teachings can include a *Cryptococcus neoformans* strain blocked for chitosan production. In various aspects, a vaccine of the present teachings can include a *Cryptococcus neoformans* strain deficient for chitosan. In various embodiments, a *Cryptococcus neoformans* strain deficient for chitosan production can confer immunity to a mammal.

In various configurations, a *Cryptococcus gattii* strain deficient for chitosan production can have one or more genetic mutations in genes encoding chitin deacetylase (cda). In some aspects, the one or more genetic mutations can reduce or eliminate the ability of the fungus to produce chitosan. In some aspects, a genetic mutation can be a deletion. In various configurations, a *Cryptococcus gattii* strain deficient for chitosan production can have one or more genetic lesions of one or more cda genes. A genetic lesion of the present teachings can include a deletion, a point mutation, an insertion mutation, and/or a frameshift mutation of any cda gene, such as, for example and without limitation, a cda1 gene, a cda2 gene, and/or a cda3 gene, or any combination thereof. In various configurations, a genetic mutation can reduce or eliminate expression of a functional cda gene product. In some configurations, a genetic deletion can reduce or eliminate expression of a cda gene. In various configurations, a *Cryptococcus gattii* strain of the present teachings can have deletions and/or inactivating mutations in the cda1 gene, the cda2 gene, the cda3 gene, a combination of mutations in the cda1 and cda2 genes, the cda1 and cda3 genes, the cda2 and cda3 genes, or the cda1, cda2 and cda3 genes.

In various configurations, a *Cryptococcus gattii* strain deficient for chitosan production that can be used in a vaccine can be a viable *Cryptococcus gattii* strain deficient for chitosan production, or an inactivated *Cryptococcus*

*gattii* strain deficient for chitosan production. In some configurations, an inactivated *Cryptococcus gattii* strain deficient for chitosan production can comprise heat-killed or heat-attenuated *Cryptococcus gattii* deficient for chitosan production. In some embodiments, a vaccine of the present teachings can include a *Cryptococcus gattii* strain blocked for chitosan production.

In various embodiments, the inventors disclose methods of conferring immunity against *Cryptococcus gattii* infection. In various configurations, these methods include pulmonary administration of an immune response-inducing amount of a *Cryptococcus gattii* strain deficient for chitosan production. In various configurations, these methods include nasal administration of a *Cryptococcus gattii* strain deficient for chitosan production. In various configurations, a *Cryptococcus gattii* strain deficient for chitosan production can be administered to the lungs of a subject via inhalation of the *Cryptococcus gattii* via the nose or mouth. In various configurations, administration of a *Cryptococcus gattii* strain deficient for chitosan production for inhalation can be accomplished using pharmaceutically acceptable means, such as, without limitation, nose drops or nasal spray.

In various embodiments, a subject that can be vaccinated against *Cryptococcus gattii* can be a human. In various embodiments, a subject that can be vaccinated against *Cryptococcus gattii* can be a non-human mammal, such as, without limitation, a dog, a cat, a camelid such as an alpaca or a llama, a rodent such as a laboratory mouse, or a farm animal such as an equine, a bovine, a caprine or an ovine.

In some embodiments, the present teachings include a vaccine against a *Cryptococcus* fungus such as *C. neoformans* or *C. gattii* which can be effective for protecting humans and various non-human animals against a *Cryptococcus* infection such as *Cryptococcus neoformans* and/or *Cryptococcus gattii* infection. In various aspects, the present teachings can include methods of inducing immunity against a *Cryptococcus* fungus. In various configurations, these methods comprise administering to a subject by inhalation an immunity-inducing amount of a composition comprising a *Cryptococcus* fungus deficient for chitosan. The *Cryptococcus* fungus can be a wild type *Cryptococcus* fungus deficient for chitosan. The *Cryptococcus* fungus deficient for chitosan can comprise, consist of, or consist essentially of no more than 60%, 55%, 50%, 45%, 40%, 35%, 30%, 25%, 20%, 15%, 10%, 9%, 8%, 7%, 6%, 5%, 4%, 3%, 2%, or 1% of the chitosan level compared to a wild type *Cryptococcus* grown on yeast extract peptone dextrose (YPD). The *Cryptococcus* fungus deficient for chitosan can be a *Cryptococcus* fungus grown in yeast nitrogen base (YNB) medium. The yeast nitrogen base (YNB) medium can be buffered to pH 7.0. In some configurations, the yeast nitrogen base (YNB) medium can be buffered to pH 7.0 with a buffering agent such as, without limitation 3-(N-morpholino)propanesulfonic acid (MOPS). In some aspects, the *Cryptococcus* fungus deficient for chitosan can be a *Cryptococcus neoformans* fungus deficient for chitosan. In some aspects, the *Cryptococcus* fungus deficient for chitosan can be a *Cryptococcus gattii* fungus deficient for chitosan. In some aspects, the *Cryptococcus* fungus deficient for chitosan can be a viable *Cryptococcus* fungus deficient for chitosan. In some aspects, the *Cryptococcus* fungus deficient for chitosan can be an inactivated *Cryptococcus* fungus deficient for chitosan. In some aspects, the *Cryptococcus* fungus deficient for chitosan can be a *Cryptococcus* fungus deleted for at least one chitin deacetylase gene. In some aspects, the at least one chitin deacetylase gene can be selected from the group consisting of cda1Δ, cda2Δ and cda3Δ. In various aspects, the *Cryptococcus* fungus deficient for chitosan can be a *Cryptococcus* fungus deleted for at least two chitin deacetylase genes. In some aspects, the at least two chitin deacetylase gene deletions can be selected from the group consisting of cda1Δcda2Δ, cda1Δcda3Δ and cda2Δcda3Δ. In some aspects, the *Cryptococcus* fungus deficient for chitosan can be a *Cryptococcus* fungus deleted for at least three chitin deacetylase genes. In some aspects, the *Cryptococcus* fungus deficient for chitosan can be a *Cryptococcus* fungus cda1Δcda2Δcda3Δ. The *Cryptococcus* fungus deficient for chitosan can be a *Cryptococcus* fungus deleted for at least a chitin synthase (chs) gene. In some aspects, the *Cryptococcus* fungus deficient for chitosan can be a *Cryptococcus* fungus chs3Δ. In some aspects, the *Cryptococcus* fungus deficient for chitosan can be a *Cryptococcus* fungus deleted for al least one chitin synthase regulator (csr) gene. In some aspects, the *Cryptococcus* fungus deficient for chitosan production can be a *Cryptococcus* fungus csr2Δ. In various aspects, the *Cryptococcus* fungus deficient for chitosan production can comprise, consist of, or consist essentially of a deletion or an inactivating mutation in at least one gene selected from the group consisting of cda1, cda2, cda3, chs3 and csr2. The administering by inhalation can comprise nasal inhalation. In some aspects, administration by nasal inhalation can be selected from the group consisting of inhaling a nose drop formulation and inhaling a nasal spray formulation.

In various embodiments, a vaccine against *Cryptococcus neoformans* infection can comprise an inactivated *Cryptococcus neoformans* strain deficient for chitosan production. In some aspects, the *Cryptococcus neoformans* strain deficient for chitosan production can be an inactivated *Cryptococcus neoformans* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus neoformans* strain deficient for chitosan production can be an inactivated *Cryptococcus neoformans* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus neoformans* strain deficient for chitosan production can be an inactivated *Cryptococcus neoformans* strain deleted for at least three chitin deacetylase (cda) genes. In some aspects, the *Cryptococcus neoformans* strain deficient for chitosan production can be an inactivated *Cryptococcus neoformans* strain cda1Δcda2Δcda3Δ. In some aspects, the *Cryptococcus neoformans* strain deficient for chitosan production can be an inactivated *Cryptococcus neoformans* strain deleted for at least a chitin synthase (chs) gene, such as, without limitation, CHS3. In some aspects, the *Cryptococcus neoformans* strain deficient for chitosan production can be an inactivated *Cryptococcus neoformans* strain chs3Δ. In some aspects, the *Cryptococcus neoformans* strain deficient for chitosan production can be an inactivated *Cryptococcus neoformans* strain deleted for at least a chitin synthase regulator (csr) gene such as, without limitation, CSR2. In some aspects, the *Cryptococcus neoformans* strain deficient for chitosan production can be an inactivated *Cryptococcus neoformans* strain csr2Δ. In some aspects, the *Cryptococcus neoformans* strain deficient for chitosan production can comprise a deletion or an inactivating mutation in one or more genes selected from the group consisting of cda1, cda2, cda3, chs3 and csr2. In some aspects, the inactivated *Cryptococcus neoformans* strain deficient for chitosan production can be a heat-killed *Cryptococcus neoformans* strain deficient for chitosan production. In some aspects, the inactivated *Cryptococcus neoformans* strain deficient for chitosan production can be a UV radiation-killed *Cryptococcus neoformans* strain deficient for chitosan production. In some aspects, the inactivated *Cryptococcus neoformans* strain deficient for chitosan production can be a *Cryptococcus neoformans* strain deficient for chitosan production inactivated by alpha-, beta-, or gamma-ray radiation. In some aspects, the inactivated *Cryptococcus neoformans* strain deficient for chitosan production can be a *Cryptococcus neoformans* strain deficient for chitosan production inactivated by photodynamic inactivation (Rodrigues, C. B., et al., Photochemistry and Photobiology 88:440-447 (2012), Fuchs, B. B., et al., Antimicrobial Agents and Chemotherapy 51: 2929-2936 (2007)). In some aspects, the vaccine against *Cryptococcus neoformans* infection can further comprise a pharmaceutically acceptable vehicle for inhalation administration. In some aspects, the pharmaceutically acceptable vehicle can comprise a buffer. In some aspects, the pharmaceutically acceptable vehicle can be a phosphate-buffered saline.

In various embodiments, a vaccine against *Cryptococcus neoformans* can comprise a viable *Cryptococcus neoformans* strain deficient for chitosan production and a pharmaceutically acceptable vehicle for inhalation administration. In some aspects, the *Cryptococcus neoformans* strain deficient for chitosan production can be a viable *Cryptococcus neoformans* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus neoformans* strain deficient for chitosan production can be a viable *Cryptococcus neoformans* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus neoformans* strain deficient for chitosan production can be a viable *Cryptococcus neoformans* strain deleted for at least three chitin deacetylase (cda) genes. In some aspects, the *Cryptococcus neoformans* strain deficient for chitosan production can be a viable *Cryptococcus neoformans* strain cda1Δcda2Δcda3Δ. In some aspects, the *Cryptococcus neoformans* strain deficient for chitosan production can be a viable *Cryptococcus neoformans* strain deleted for at least one chitin synthase such as, without limitation, CHS3. In some aspects, the *Cryptococcus neoformans* strain deficient for chitosan production can be a viable *Cryptococcus neoformans* strain chs3Δ. In some aspects, the *Cryptococcus neoformans* strain deficient for chitosan production can be a viable *Cryptococcus neoformans* strain deleted for at least a chitin synthase regulator (CSR2). In some aspects, the *Cryptococcus neoformans* strain deficient for chitosan production can comprise a viable *Cryptococcus neoformans* strain csr2Δ. In some aspects, the pharmaceutically acceptable vehicle can comprise a buffer. In some aspects, the pharmaceutically acceptable vehicle can comprise phosphate-buffered saline.

In various embodiments, a pharmaceutically acceptable composition for a vaccine against *Cryptococcus neoformans* infection of the present teachings can comprise the inactivated *Cryptococcus neoformans* strain deficient for chitosan production in a nose drop formulation. In some aspects, a pharmaceutically acceptable composition for a vaccine against *Cryptococcus neoformans* infection of the present teachings can comprise an inactivated *Cryptococcus neoformans* strain deficient for chitosan production in a nasal spray formulation.

In various embodiments, methods of inducing immunity against *Cryptococcus neoformans*, can comprise administering to a subject by inhalation an immunity-inducing amount of a composition of the present teachings. In some aspects, the administering by inhalation can comprise nasal inhalation.

In various embodiments, a vaccine against *Cryptococcus neoformans* infection can comprise a viable *Cryptococcus neoformans* strain deficient for chitosan production. In some aspects, the *Cryptococcus neoformans* strain deficient for chitosan production can be a viable *Cryptococcus neoformans* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus neoformans* strain deficient for chitosan production can be a viable *Cryptococcus neoformans* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3←. In some aspects, the *Cryptococcus neoformans* strain deficient for chitosan production can be a viable *Cryptococcus neoformans* strain deleted for at least three chitin deacetylase (cda) genes. In some aspects, the *Cryptococcus neoformans* strain deficient for chitosan production can be a viable *Cryptococcus neoformans* strain cda1Δcda2Δcda3Δ. In some aspects, the *Cryptococcus neoformans* strain deficient for chitosan production can be a viable *Cryptococcus neoformans* strain chs3Δ. In some aspects, the *Cryptococcus neoformans* strain deficient for chitosan production can be a viable *Cryptococcus neoformans* strain csr2Δ. In some aspects, the *Cryptococcus neoformans* strain deficient for chitosan production can be a viable *Cryptococcus neoformans* strain chs3Δ csr2Δ. In some aspects, the *Cryptococcus neoformans* strain deficient for chitosan production can be a viable *Cryptococcus neoformans* strain cda1Δ chs3Δ csr2Δ. A vaccine against *Cryptococcus neoformans* infection of the present teachings can further comprise a pharmaceutically acceptable vehicle for inhalation administration. In some aspects, the pharmaceutically acceptable vehicle can comprise a buffer. In some aspects, the pharmaceutically acceptable vehicle can comprise phosphate-buffered saline.

In various embodiments, a vaccine against *Cryptococcus neoformans* can comprise a viable *Cryptococcus neoformans* strain deficient for chitosan production and a pharmaceutically acceptable vehicle tor inhalation administration. In some aspects, the *Cryptococcus neoformans* strain deficient for chitosan production can be a viable *Cryptococcus neoformans* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus neoformans* strain deficient for chitosan production can be a viable *Cryptococcus neoformans* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus neoformans* strain deficient for chitosan production can be a viable *Cryptococcus neoformans* strain deleted for at least three chitin deacetylase (cda) genes. In some aspects, the *Cryptococcus neoformans* strain deficient for chitosan production can be a viable *Cryptococ-

*cus neoformans* strain cda1Δcda2Δcda3Δ. In some aspects, the *Cryptococcus neoformans* strain deficient for chitosan production can be a viable *Cryptococcus neoformans* strain chs3Δ. In some aspects, the *Cryptococcus neoformans* strain deficient for chitosan production can be a viable *Cryptococcus neoformans* strain car2Δ. In some aspects, the *Cryptococcus neoformans* strain deficient for chitosan production can be a viable *Cryptococcus neoformans* strain cda1 cda2 cda3 chs3 csr2. In some aspects, the pharmaceutically acceptable vehicle can comprise a buffer. In some aspects, the pharmaceutically acceptable vehicle can be a phosphate-buffered saline.

In various embodiments, a pharmaceutically acceptable composition for a vaccine against *Cryptococcus neoformans* infection can comprise the viable *Cryptococcus neoformans* strain deficient for chitosan production of the present teachings in a nose drop formulation. In some aspects, the pharmaceutically acceptable composition for a vaccine against *Cryptococcus neoformans* infection can comprise the viable *Cryptococcus neoformans* strain deficient for chitosan production of the present teachings in a nasal spray formulation.

In various embodiments, methods of inducing immunity against *Cryptococcus neoformans* can comprise administering to a subject by inhalation an immunity-inducing amount of a composition comprising a viable *Cryptococcus neoformans* strain deficient for chitosan production of the present teachings. In some aspects, the administering by inhalation can comprise nasal inhalation.

In various embodiments, the present teachings include a vaccine against *Cryptococcus gattii* infection, comprising an inactivated *Cryptococcus gattii* strain deficient for chitosan production. In various configurations, the *Cryptococcus gattii* strain deficient for chitosan production can be an inactivated *Cryptococcus gattii* strain deleted for at least one chitin deacetylase (cda) gene. In various aspects, at least one chitin deacetylase (cda) gene deletion can be selected from the group consisting of cda1Δ, cda2Δ and cda3Δ. In some aspects, a *Cryptococcus gattii* strain deficient for chitosan production can be an inactivated *Cryptococcus gattii* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus gattii* strain deficient for chitosan production can be an inactivated *Cryptococcus gattii* strain deleted for at least three chitin deacetylase (cda) genes. In some aspects, the *Cryptococcus gattii* strain deficient for chitosan production can be an inactivated *Cryptococcus gattii* strain cda1Δcda2Δcda3Δ. In some aspects, the inactivated *Cryptococcus gattii* strain deficient for chitosan production can be a heat-killed *Cryptococcus gattii* strain deficient for chitosan production. In some configurations, a vaccine against *Cryptococcus gattii* infection of the present teachings can further comprise a pharmaceutically acceptable vehicle for inhalation administration. In some aspects, the pharmaceutically acceptable vehicle can comprise a buffer. In some aspects, the pharmaceutically acceptable vehicle can be a phosphate-buffered saline.

In various embodiments, a vaccine against *Cryptococcus gattii* can comprise a viable *Cryptococcus gattii* strain deficient for chitosan production and a pharmaceutically acceptable vehicle for inhalation administration. In some aspects, the *Cryptococcus gattii* strain deficient for chitosan production can be a viable *Cryptococcus gattii* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus gattii* strain deficient for chitosan production can be a viable *Cryptococcus gattii* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus gattii* strain deficient for chitosan production can be a viable *Cryptococcus gattii* strain deleted for at least three chitin deacetylase (cda) genes. In some aspects, the *Cryptococcus gattii* strain deficient for chitosan production can be a viable *Cryptococcus gattii* strain cda1Δcda2Δcda3Δ. In some aspects, the pharmaceutically acceptable vehicle can comprise a buffer. In some aspects, the pharmaceutically acceptable vehicle can be a phosphate-buffered saline.

In various embodiments, a pharmaceutically acceptable composition for a vaccine against *Cryptococcus gattii* infection can comprise the inactivated *Cryptococcus gattii* strain deficient for chitosan production of the present teachings in a nose drop formulation. In various embodiments, the pharmaceutically acceptable composition for a vaccine against *Cryptococcus gattii* infection can comprise the inactivated *Cryptococcus gattii* strain deficient for chitosan production of the present teachings in a nasal spray formulation.

In various embodiments, methods of inducing immunity against *Cryptococcus gatti* can comprise administering to a subject by inhalation an immunity-inducing amount of a composition comprised by an inactivated *Cryptococcus gattii* strain deficient for chitosan production of the present teachings. In some aspects, the administering by inhalation can comprises nasal inhalation.

In various embodiments, a vaccine against *Cryptococcus gattii* infection can comprise a viable *Cryptococcus gattii* strain deficient for chitosan production. In some aspects, the *Cryptococcus gattii* strain deficient for chitosan production can be a viable *Cryptococcus gattii* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus gattii* strain deficient for chitosan production can be a viable *Cryptococcus gattii* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus gattii* strain deficient for chitosan production can be a viable *Cryptococcus gattii* strain deleted for at least three chitin deacetylase (cda) genes. In some aspects, the *Cryptococcus gattii* strain deficient for chitosan production can be a viable *Cryptococcus gattii* strain cda1Δcda2Δcda3Δ. In some aspects, the viable *Cryptococcus gattii* strain deficient for chitosan production can be a heat-killed *Cryptococcus gattii* strain deficient for chitosan production. In some aspects, a vaccine against *Cryptococcus gattii* infection of the present teachings can further comprise a pharmaceutically acceptable vehicle for inhalation administration. In some aspects, the pharmaceutically acceptable vehicle can comprise a buffer. In some aspects, the pharmaceutically acceptable vehicle can be a phosphate-buffered saline.

In various embodiments, a vaccine against *Cryptococcus gattii* can comprise a viable *Cryptococcus gattii* strain deficient for chitosan production and a pharmaceutically acceptable vehicle for inhalation administration. In some aspects, the *Cryptococcus gattii* strain deficient for chitosan production can be a viable *Cryptococcus gattii* strain deleted for at least one chitin deacetylase (cda) gene. In some aspects, the at least one chitin deacetylase (cda) gene deletion can be selected from the group consisting of cda1Δ, cda2Δ and cda3Δ. In some aspects, the *Cryptococcus gattii* strain deficient for chitosan production is a viable *Cryptococcus gattii* strain deleted for at least two chitin deacetylase (cda) genes. In some aspects, the at least two chitin deacetylase (cda) gene deletions can be selected from the group consisting of cda1Δcda2Δ, cda1Δcda3Δ and cda2Δcda3Δ. In some aspects, the *Cryptococcus gattii* strain deficient for chitosan production can be a viable *Cryptococcus gattii* strain deleted for at least three chitin deacetylase (cda) genes. In some aspects, the *Cryptococcus gattii* strain deficient for chitosan production can be a viable *Cryptococcus gattii* strain cda1Δcda2Δcda3Δ. In some aspects, the pharmaceutically acceptable vehicle can comprise a buffer. In some aspects, the pharmaceutically acceptable vehicle can comprise phosphate-buffered saline. In some aspects, the pharmaceutically acceptable composition for a vaccine against *Cryptococcus gattii* infection can comprise the viable *Cryptococcus gattii* strain deficient for chitosan production of the present teachings in a nose drop formulation. In some aspects, a pharmaceutically acceptable composition for a vaccine against *Cryptococcus gattii* infection can comprise the viable *Cryptococcus gattii* strain deficient for chitosan production of the present teachings in a nasal spray formulation. In some aspects, a method of inducing immunity against *Cryptococcus gattii* can comprise administering to a subject by inhalation an immunity-inducing amount of a composition comprised by a viable *Cryptococcus gattii* strain deficient for chitosan production. In some aspects, the administering by inhalation can comprise nasal inhalation.

DETAILED DESCRIPTION

Figure 1A:
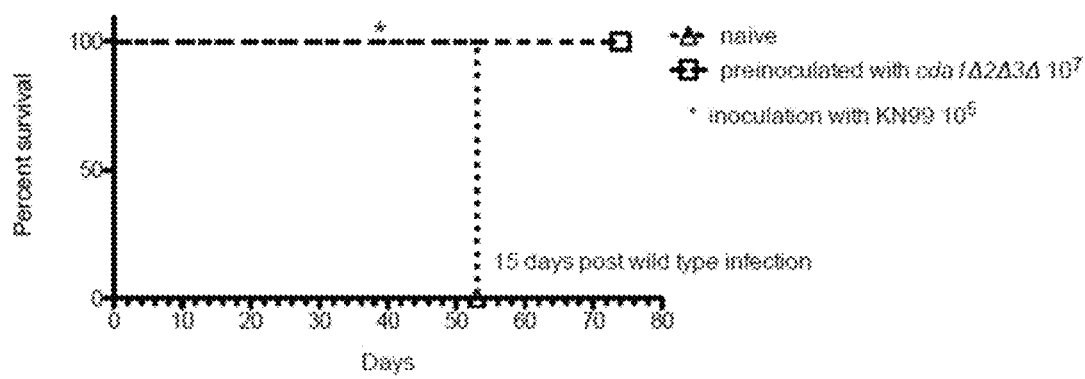
FIG. 1A-B illustrate that mice exposed to *Cryptococcus neoformans* cda1Δcda2Δcda3Δ survive wild type *Cryptococcus neoformans* infection.

The present inventors have developed vaccines and administration protocols against infection by *Cryptococcus* fungi, including *Cryptococcus neoformans* and *Cryptococcus gattii*. In various embodiments, a vaccine of the present teachings can provide significant protection against exposure to a virulent *Cryptococcus* strain, such as a wild type *Cryptococcus neoformans* or *Cryptococcus gattii*, up to 100% protection.

As used herein, an "inactivated" *Cryptococcus* refers to a *Cryptococcus* fungus that has been disabled or killed such that it is unable to reproduce upon infection of a host organism, or grow in a standard nutrient medium. Inactivation of a *Cryptococcus*, including *Cryptococcus* deficient for chitosan production, can be accomplished by any method known to skilled artisans. In various configurations, an inactivated *Cryptococcus* fungus of the present teachings can comprise heat-killed or heat-attenuated *Cryptococcus*, such as but not limited to heat-killed *C. neoformans* cda1Δ, *C. neoformans* cda2ΔC. neoformans cda3Δ, *C. neoformans* chs3Δ, *C. neoformans* csr2Δ or any combination thereof, such as, without limitation *C. neoformans* cda1Δcda2Δcda3Δ. In various configurations, an inactivated *Cryptococcus* fungus of the present teachings can comprise heat-killed or heat-attenuated *Cryptococcus*, such as but not limited to heat-killed *C. gattii* cda1Δ, *C. gattii* cda2Δ *C. gattii* cda3Δ, *C. gattii* chs3Δ, *C. gattii* csr2Δ or any combination thereof, such as, without limitation *C. gattii* cda1Δcda2Δcda3Δ. In some configurations, an inactivated *Cryptococcus* strain deficient for chitosan production can comprise *Cryptococcus* that is deficient for chitosan production and has been killed by exposure to heat, to electromagnetic radiation such as ultraviolet light, gamma ray radiation, or x-ray radiation, by exposure to nuclear radiation such as exposure to an alpha particle emitting source or a beta particle emitting source, by exposure to toxic levels of one or more chemicals, by photodynamic inactivation (Rodrigues, G. B., et al., Photochemistry and Photobiology 88:440-447, 2012; Fuchs, B. B., et al., Antimicrobial Agents and Chemotherapy 51: 2929-2936, 2007), or any combination thereof. In some configurations, effectiveness of an inactivating treatment can be tested by plating treated samples on nutrient plates under standard conditions; a treatment can be considered inactivating if no colony forming units develop.

Methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Nagy, A., Manipulating the Mouse Embryo: A Laboratory Manual (Third Edition), Cold Spring Harbor, N.Y., 2003 and Harlow, E., Using Antibodies: A Laboratory Manual, Cold Spring Harbor Laboratory Press, Cold Spring Harbor, N.Y., 1999. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. As used in the present description and any appended claims, the singular forms "a", "an" and "the" are intended to include the plural forms as well, unless the context indicates otherwise.

In various embodiments, a *Cryptococcus* fungus, including without limitation *Cryptococcus neoformans* or *Cryptococcus gattii* comprising mutations in at least one, at least two, or at least three chitin deacetylase (cda)genes and/or chitin synthase genes and/or chitin synthase regulator genes can be obtained and grown by established procedures (See, e.g., Baker, L. G., et al., *Eukaryotic Cell* 6: 855-867, 2007 and Baker, L. G., et al., *Eukaryotic Cell* 10: 1264-1268, 2011). A mutation can interfere with, inactivate, or eliminate a gene or its encoded protein product. In various embodiments, a *Cryptococcus* fungus, including without limitation either *Cryptococcus neoformans* or *Cryptococcus gattii* of the present teachings deficient for chitosan can be obtained and grown by established procedures.

In various embodiments, *Cryptococcus neoformans* strains of the present teachings can comprise the following DNA sequences.

*C. neoformans* CDA1 (CNAG_05799):

Wild type gene: Bolded regions are predicted introns. The sequences between the double-underlined sequences are deleted in the deletion strain. GGCCCTCTACTCTACCTTCG (SEQ ID No:1) and GCCGCCTCTAACACTTCTTCC (SEQ ID No:2) are the primer sequences used for deletion. The residues in bold and italicized typeface are the sites used for creating active site mutants. In some configurations, selectable markers (not indicated) can be inserted in place of the deleted portions.

(SEQ ID No.: 3)

GCCGAACAGCGCAGGTCAGGGAGAGCATTTCTAGCGTGCCTTGGTAGATCGTTATCGCGATT

TACTTTCCAGGCCCTGGGCGCTTCCAGCCATCAGCCAAAGGATAAAAGCGCGTGCCCTCTTC

TTTTCATCATTAACTTTTATCCTCCTCAGCACCCACGCTCTGTGATTCCATCTCTTCCTCCT

CGCATTCAAGCAGCCTCTTCATTTCTTTCCTCCGTCCCGGTGAGTGCGACGCCCGCCGCTGC

CATTCCCACACGATGACTTGAGACGCGTCTTCCCGCTATAGCCGACGCCCCTTTTCGTTTTC

TTGGCGTTTTGTCACATTGCCACATTGAGCAGCACAGCTTACTTGTCAGCAGCAAAAATCCA

ACTTCAAACAGCTCTTCAGCATCAACTCTATCACTCTTTCATCTCTTGTCAACTTCTCTTCC

TTCTCGCTCCAAAAGCGGAATTTCGCC *ATG*TTTACATTCGCTGCCTTCTCTGCTCTTCTAAT

TTCCCTCGCTGGTGTGGTGGCGCAGACTACAGGCACATCGGTTGACAGTAGCATCTTAACTA

AGACTGCTGACTCTACCGGTCCCTCTGGTTTCTCCATTCCGTGAGTACTCTCGACTTTTCCG

TCAACCTCCAGTCTCGCCACAGGCCATAGCGAACAATGAGCCAAGCGCCCACGCGAACCGTG

CCCATCATTATCCTCCCACTAATTCCTTTAACCAAACGTAGCTTTTAGAGGCCAAATGCTGA

CAAGTGCGTTTTTAGTGCTTTGAGCGAGCTCACGTCTGGTGCCCCCACTGACTCTACTGTGG

CCCTCTACTCTACCTTCGCGGCCGGTGCCACACCTACCGTTTCTGGTGCCCCTGTCCTCCCT

ACCAGTGCCCTCACCATCGCCGATTATCCAGCTTTAGATGTCACCCCTCCTACCAACTCCTC

TTTGGTTAAGGACTGGATGGCCAAGGTGAGTTGTGTTTGAGTCCGAAAAGGCACCAGAAGAG

CTAACAGTTGGATTAGATCGACTTGTCCAAGGTGCCCAGTTATAATGTGACAACGGGCGATT

GTTCTACTGACGCGGCTGCTATCAGCGACGGTCGATGCTGGTGGACTTGTGGTGGTTGCACT

CGGGAAACCGACATTGTCGAGTGTCCTGACAAGAATGTTTGGGGTCTCTCTTAC *GATGAT*GG

TCTTCGTTGTCGGCTCTCGTGTCCTTTCTCGACCCGAGATGCTCCAAACCGAATACATGTCT

GGACACCAGATCTCTATCCACACTTGGTCTCACCCCGCACTTACTACTCTTACCAACGAGGA

AATTGTTGCCGAGCTTGGTTGGACAATGAAGGTCATCAAGGACACCCTTGGCGTCACCCCAA

ACACTTTC *CGA*CCCCCTTATGGTGACATTGATGACCGTGTTCGAGCTATTGCTGCTCAGATG

GGCTTGACCCCTGTTATCTGGACTTCTTACACTGATGGCTCAACCACTGTTAACTTTGACAC

TGTAGGCTTATCTTGACTTTCGCAATAATCTTACTAACGAAATGACAGAAC *GAC*TGGCACAT

CAGTGGTGGTACCGCCACCGGCGCTTCTTCTTATGAGACCTTTGAGAAGATTCTCACCGAAT

ACGCCCCAAAGTTGGACACTGGTTTCATCACTCTTGAGCACGACAGTAAGTCTTGTCTATCC

GTCTTGCAATAATAATCCTGACGTATACCTTTACAGTCTACCAGCAGAGTGTTGACCTTGCT

GTTGGTTACATTTTGCCCCAAGTTCTCGCCAACGGTACCTATCAGCTCAAATCCATCATCAA

```
CTGTTTGGGCAAGGACAGTAAGTTGCCTCCGCTAATCAGAAAAGGTTGTGGGCTAAGATGAT

ACACAGCCTCCGAAGCATACATTGAGACTTCATCCAACCAGACTACTACTCAGATCACTGCA

GCCACCGGCTCCCAGTCTACCTTCTTCCAGCCCATTGTTGGCACTGCTACCGGTGCTGAAGT

CTCTGCACCTTCTGAGGCCACTGGCAGCACTGCCGCTGGCTCTGCTGCCTCCACCACTAGTG

GTTCTGGCGCCAGCGCTTCTACAGGCGCCGCCTCTAACACTTCTTCCAGCGGGTCTGGTCGA

TCAGCCACCATGGGTGGTGCCCTCATTGCTCTTGCCGCTGTTGCGGTTGGTATGGTATATGT

CGCC TAAGTATTTCAAGGCTTTCAATGTAACGATGGATGGGGATGGGTGGTGGGGGGGAGG

GAAGTGTGTCTAATGGGGCTATACTTGGGCTATACTTTGCCTCAAATCCATCAAGTATTAAT

AGCTGAACCATCTTTCGTTGAACCGTCTTTCATTGTGAACCATTTGTCTTTTTGATCTTTCA

AAGTTTGATCCATTATGAATATCATGGACATTTTGAACGTTTTGAACATCCATGTACTTTTC

ATTCGATCGATCTGAACGTGTTGTTGTGCATACCTCGCGAACAAGCTTTCAATGGATGGCTT

CAC
```

Mutant A is a triple point mutant that can be D166, R254 and D 294-catalytically inactive mutant:

The sequence of the mutant gene can comprise the mutated residues:

(SEQ ID No.: 4)
```
GCCGAACAGCGCAGGTCAGGGAGAGCATTTCTAGCGTGCCTTGGTAGATCGTTATCGCGATT

TACTTTCCAGGCCCTGGGCGCTTCCAGCCATCAGCCAAAGGATAAAAGCGCGTGCCCTCTTC

TTTTCATCATTAACTTTTATCCTCCTCAGCACCCACGCTCTGTGATTCCATCTCTTCCTCCT

CGCATTCAAGCAGCCTCTTCATTTCTTTCCTCCGTCCCGGTGAGTGCGACGCCCGCCGCTGC

CATTCCCACACGATGACTTGAGACGCGTCTTCCCGCTATAGCCGACGCCCCTTTTCGTTTTC

TTGGCGTTTTGTCACATTGCCACATTGAGCAGCACAGCTTACTTGTCAGCAGCAAAAATCCA

ACTTCAAACAGCTCTTCAGCATCAACTCTATCACTCTTTCATCTCTTGTCAACTTCTCTTCC

TTCTCGCTCCAAAAGCGGAATTTCGCC ATGTTTACATTCGCTGCCTTCTCTGCTCTTCTAAT

TTCCCTCGCTGGTGTGGTGGCGCAGACTACAGGCACATCGGTTGACAGTAGCATCTTAACTA

AGACTGCTGACTCTACCGGTCCCTCTGGTTTCTCCATTCCGTGAGTACTCTCGACTTTTCCG

TCAACCTCCAGTCTCGCCACAGGCCATAGCGAACAATGAGCCAAGCGCCCACGCGAACCGTG

CCCATCATTATCCTCCCACTAATTCCTTTAACCAAACGTAGCTTTTAGAGGCCAAATGCTGA

CAAGTGCGTTTTTAGTGCTTTGAGCGAGCTCACGTCTGGTGCCCCCACTGACTCTACTGTGG

CCCTCTACTCTACCTTCGCGGCCGGTGCCACACCTACCGTTTCTGGTGCCCCTGTCCTCCCT

ACCAGTGCCCTCACCATCGCCGATTATCCAGCTTTAGATGTCACCCCTCCTACCAACTCCTC

TTTGGTTAAGGACTGGATGGCCAAGGTGAGTTGTGTTTGAGTCCGAAAAGGCACCAGAAGAG

CTAACAGTTGGATTAGATCGACTTGTCCAAGGTGCCCAGTTATAATGTGACAACGGGCGATT

GTTCTACTGACGCGGCTGCTATCAGCGACGGTCGATGCTGGTGGACTTGTGGTGGTTGCACT

CGGGAAACCGACATTGTCGAGTGTCCTGACAAGAATGTTTGGGGTCTCTCTTAC AACGATGG

GCCTTCTCCCTTCACCCCTCTCCTAATTGATTACCTTCAGGAGAAGAACATCAAGACCACCT

TCTTCGTTGTCGGCTCTCGTGTCCTTTCTCGACCCGAGATGCTCCAAACCGAATACATGTCT

GGACACCAGATCTCTATCCACACTTGGTCTCACCCCGCACTTACTACTCTTACCAACGAGGA

AATTGTTGCCGAGCTTGGTTGGACAATGAAGGTCATCAAGGACACCCTTGGCGTCACCCCAA

ACACTTTC GCTCCCCCTTATGGTGACATTGATGACCGTGTTCGAGCTATTGCTGCTCAGATG
```

-continued
```
GGCTTGACCCCTGTTATCTGGACTTCTTACACTGATGGCTCAACCACTGTTAACTTTGACAC

TGTAGGCTTATCTTGACTTTCGCAATAATCTTACTAACGAAATGACAGAAC AACTGGCACAT

CAGTGGTGGTACCGCCACCGGCGCTTCTTCTTATGAGACCTTTGAGAAGATTCTCACCGAAT

ACGCCCCAAAGTTGGACACTGGTTTCATCACTCTTGAGCACGACAGTAAGTCTTGTCTATCC

GTCTTGCAATAATAATCCTGACGTATACCTTTACAGTCTACCAGCAGAGTGTTGACCTTGCT

GTTGGTTACATTTTGCCCCAAGTTCTCGCCAACGGTACCTATCAGCTCAAATCCATCATCAA

CTGTTTGGGCAAGGACAGTAAGTTGCCTCCGCTAATCAGAAAAGGTTGTGGGCTAAGATGAT

ACACAGCCTCCGAAGCATACATTGAGACTTCATCCAACCAGACTACTACTCAGATCACTGCA

GCCACCGGCTCCCAGTCTACCTTCTTCCAGCCCATTGTTGGCACTGCTACCGGTGCTGAAGT

CTCTGCACCTTCTGAGGCCACTGGCAGCACTGCCGCTGGCTCTGCTGCCTCCACCACTAGTG

GTTCTGGCGCCAGCGCTTCTACAGGCGCCGCCTCTAACACTTCTTCCAGCGGGTCTGGTCGA

TCAGCCACCATGGGTGGTGCCCTCATTGCTCTTGCCGCTGTTGCGGTTGGTATGGTATATGT

CGCC TAAGTATTTCAAGGCTTTCAATGTAACGATGGATGGGGATGGGTGGTGGGGGGGAGG

GAAGTGTGTCTAATGGGGCTATACTTGGGCTATACTTTGCCTCAAATCCATCAAGTATTAAT

AGCTGAACCATCTTTCGTTGAACCGTCTTTCATTGTGAACCATTTGTCTTTTTGATCTTTCA

AAGTTTGATCCATTATGAATATCATGGACATTTTGAACGTTTTGAACATCCATGTACTTTTC

ATTCGATCGATCTGAACGTGTTGTTGTGCATACCTCGCGAACAAGCTTTCAATGGATGGCTT

CAC
```

Mutant B is a mutant in which the potential Zinc binding site viz: D167, H216 and H220 are mutated.

(SEQ ID No.: 5)
```
GGAACAATAACAAAGCACAACGCGACAAAAGCCGAACAGCGCAGGTCAGGGAGAGCATTTCT

AGCGTGCCTTGGTAGATCGTTATCGCGATTTACTTTCCAGGCCCTGGGCGCTTCCAGCCATC

AGCCAAAGGATAAAAGCGCGTGCCCTCTTCTTTTCATCATTAACTTTTATCCTCCTCAGCAC

CCACGCTCTGTGATTCCATCTCTTCCTCCTCGCATTCAAGCAGCCTCTTCATTTCTTTCCTC

CGTCCCGGTGAGTGCGACGCCCGCCGCTGCCATTCCCACACGATGACTTGAGACGCGTCTTC

CCGCTATAGCCGACGCCCCTTTTCGTTTTCTTGGCGTTTTGTCACATTGCCACATTGAGCAG

CACAGCTTACTTGTCAGCAGCAAAAATCCAACTTCAAACAGCTCTTCAGCATCAACTCTATC

ACTCTTTCATCTCTTGTCAACTTCTCTTCCTTCTCGCTCCAAAAGCGGAATTTCGCC ATGTT

TACATTCGCTGCCTTCTCTGCTCTTCTAATTTCCCTCGCTGGTGTGGTGGCGCAGACTACAG

GCACATCGGTTGACAGTAGCATCTTAACTAAGACTGCTGACTCTACCGGTCCCTCTGGTTTC

TCCATTCCGTGAGTACTCTCGACTTTTCCGTCAACCTCCAGTCTCGCCACAGGCCATAGCGA

ACAATGAGCCAAGCGCCCACGCGAACCGTGCCCATCATTATCCTCCCACTAATTCCTTTAAC

CAAACGTAGCTTTTAGAGGCCAAATGCTGACAAGTGCGTTTTTAGTGCTTTGAGCGAGCTCA

CGTCTGGTGCCCCCACTGACTCTACTGTGGCCCTCTACTCTACCTTCGCGGCCGGTGCCACA

CCTACCGTTTCTGGTGCCCCTGTCCTCCCTACCAGTGCCCTCACCATCGCCGATTATCCAGC

TTTAGATGTCACCCCTCCTACCAACTCCTCTTTGGTTAAGGACTGGATGGCCAAGGTGAGTT

GTGTTTGAGTCCGAAAAGGCACCAGAAGAGCTAACAGTTGGATTAGATCGACTTGTCCAAGG

TGCCCAGTTATAATGTGACAACGGGCGATTGTTCTACTGACGCGGCTGCTATCAGCGACGGT

CGATGCTGGTGGACTTGTGGTGGTTGCACTCGGGAAACCGACATTGTCGAGTGTCCTGACAA
```

-continued

```
GAATGTTTGGGGTCTCTCTTACGAT AACGGGCCTTCTCCCTTCACCCCTCTCCTAATTGATT

ACCTTCAGGAGAAGAACATCAAGACCACCTTCTTCGTTGTCGGCTCTCGTGTCCTTTCTCGA

CCCGAGATGCTCCAAACCGAATACATGTCTGGACACCAGATCTCTATC GCCACTTGGTCT GC

CCCGCACTTACTACTCTTACCAACGAGGAAATTGTTGCCGAGCTTGGTTGGACAATGAAGG

TCATCAAGGACACCCTTGGCGTCACCCCAAACACTTTCGCTCCCCCTTATGGTGACATTGAT

GACCGTGTTCGAGCTATTGCTGCTCAGATGGGCTTGACCCCTGTTATCTGGACTTCTTACAC

TGATGGCTCAACCACTGTTAACTTTGACACTGTAGGCTTATCTTGACTTTCGCAATAATCTT

ACTAACGAAATGACAGAACAACTGGCACATCAGTGGTGGTACCGCCACCGGCGCTTCTTCTT

ATGAGACCTTTGAGAAGATTCTCACCGAATACGCCCCAAAGTTGGACACTGGTTTCATCACT

CTTGAGCACGACAGTAAGTCTTGTCTATCCGTCTTGCAATAATAATCCTGACGTATACCTTT

ACAGTCTACCAGCAGAGTGTTGACCTTGCTGTTGGTTACATTTTGCCCCAAGTTCTCGCCAA

CGGTACCTATCAGCTCAAATCCATCATCAACTGTTTGGGCAAGGACAGTAAGTTGCCTCCGC

TAATCAGAAAGGTTGTGGGCTAAGATGATACACAGCCTCCGAAGCATACATTGAGACTTCA

TCCAACCAGACTACTACTCAGATCACTGCAGCCACCGGCTCCCAGTCTACCTTCTTCCAGCC

CATTGTTGGCACTGCTACCGGTGCTGAAGTCTCTGCACCTTCTGAGGCCACTGGCAGCACTG

CCGCTGGCTCTGCTGCCTCCACCACTAGTGGTTCTGGCGCCAGCGCTTCTACAGGCGCCGCC

TCTAACACTTCTTCCAGCGGGTCTGGTCGATCAGCCACCATGGGTGGTGCCCTCATTGCTCT

TGCCGCTGTTGCGGTTGGTATGGTATATGTCGCC TAAGTATTTCAAGGCTTTCAATGTAACG

ATGGATGGGATGGGTGGTGGGGGGGAGGGAAGTGTGTCTAATGGGGCTATACTTGGGCTA

TACTTTGCCTCAAATCCATCAAGTATTAATAGCTGAACCATCTTTCGTTGAACCGTCTTTCA

TTGTGAACCATTTGTCTTTTTGATCTTTCAAAGTTTGATCCATTATGAATATCATGGACATT

TTGAACGTTTTGAACATCCATGTACTTTTCATTCGATCGATCTGAACGTGTTGTTGTGCATA

CCTCGCGAACAAGCTTTCAATGGATGGCTTCACAGATC.
```

CDA2: CNAG_01230: chitin deacetylase 2: The sequences between the underlined sequences are deleted in the deletion strain.

(SEQ ID No.: 6)
```
GAAAATCACAGCACAGCAACATAACAAACCGCAAAACAAAAGGTAGAAGTAAAAATAGCAAATAGC

GCAGAATAACCGACATCGCCCTCATAAAACGAAGGCTCAAAGCTCGGCTGCTGATTCTCATTTCTCTC

ATCTCCATTCTTCTTTCTCATCGTATTACCTTTTCCGCTCTTTATCTCCAAGAACAATAATAATCTTTTCG

CCTCTTAATCACACAGGCGAA ATGATCCCTTCCACCGCCGCCGCCCTCCTCACCCTCACAGCTGGTGC

CGCCTTCGCCCATACCGGATGTGGTGGCCACGAGATTGGTCGGCGAAATGTTGGCGGTCCCATGTT

GTATCGTCGAGCTGTCACCGATGAAGCTAGTGCTGCTGTCAGTACAGGTAGGTTAATACAATACAAT

ACAATCGTATTCTATGACAATGACTGACCATAACGACCACGTAGACATCAACACCGAGTGTACAGCC

TACAGTTATGCCCCTGTGACCGAGTTGATATCCTCTTTCCCGACTATTTGGCAGACTGCTTCCATCCCC

TCCAATGACACAGAAGCCCAACAACTTTTTGGGAAAATTAACTCCACTCTTAATACCAAGATTCCAAA

TGATGTACCCCACGGAACCCCCACGGGTGATTGGACCGGTGTGAACTACTCTAACAGTGACCCGGA

CTGTTGGTGGACTCATAACAAGTGCACGACTCCTTCCAACGACACTGGTTTGCAAGCCGATATCTCC

ATCGCACCCGAGCCAATGACATGGGGTTTGGGTTTTGACGATGGACCTAACTGTAGTCACAACGCTT

TGTATGATCTTCTTTTGGAGAACAACCAGAAGGCTACCATGTACGTGATCATCTCTCTTTATTCATGTC

CAAACTTATGTATGTAAAAGGTTTTTCATTGGATCCAATGTCTTGGACTGGCCTCTCCAGGCTATGAG
```

-continued

```
GGCTCACGACGAAGGTCATGAAATATGTGTTCACACCTGGTCTCATCAATACATGACCGCCCTCAGT

AACGAGGTCGTCTTTGCCGAATTGTACTACACCCAGAAAGCCATCAAGGCTGTTCTCGGAGTTACTC

CCCAGTGCTGGTATGTTGGCACTTTGGTGGAATCGTGTGAGACTATAGCTAATGATGACACAGGCG

ACCTCCGTACGGTGATGTCGACAACAGAGTTCGTATGATTGCCGAGGGACTCAACCTGACTACCATC

ATCTGGTCAGACGACACCGATGACTGGGCGGCTGGAACCAACGGCGTCACTGAGCAAGACGTCACA

AATAACTACCAGTCAGTGATCGACAAGGCTGGTAACGGTACATACACTACTCACGGCCCCGTTGTTC

TTAACCACGAGCTCAGTAAGTCTCTCCCAACGACTAAACCGATGTTTGCTCACGATGTCCTCTTCAGC

CAACTACACCATGTCTGTCTTCATGACTATGTTCCCCAAGATCAAATCAGCTTTCAACTACATTGTCCC

CATTTGCACTGCATACAACATCACCCAACCATATGCCGAAAGTAATATCACTTGTCCCAACTTTGAAA

CTTACATCTCTGGTGTCACAAACATCAGCAGCTCTACCACTCAGAAAGATGGAAGCAGCTCAACAAA

CACTGCTTCTGGTTCCGGCGCCGCTGGTAGTGCCAGTGCCACTAGCAGCAGCGACGACTCAAGCAG

CTCTGGTGGCTCAAGCGGCTCTAGTGGCTCAAACAACGCTAGCAGTGGTGCTTTGGGCATGTTCGAC

AGTTTGTCAGGAGTGGGTCTTATTTTGGGGGGTGTAGTTGCTGGTGTGATGCTGCTG TAATGTGAT

GTGCTTTAGCACGAAAAAAATGGACAGTATATCAAACGTCACATGACGTACTATGTATCCAAACGGA

GGTTCGGGTGAGACACCCGTCAATCTAATTCIGTTAAGGGCATTTGATGATTGTCAGTTCTACGTAG

TGCCGAAACGAAGATTGAGTTTCTGTTATCTAACAGACGAAAAGGAACGCTGATATGCACTGCCATT

TATCTGAGATCCAATG
```

*C. neoformans* var. *grubii* H99 (CNA3): CNAG_01239—
chitin deacetylase: CDA3

The sequences of the primers are underlined. The sequence between the underlined primer sequences are deleted. In CDA3 deleted strains around 3049 bp of chromosomal sequence has been deleted out of which 1528 bp actually belong to CDA3 genomic region.

(SEQ ID No.: 7)
```
GGCATGTCGTGATTAATTATTTGACATTTTGTTCTATTCGTTTCAGATCCAGTAATAGTTTTTTTCTCTT

TATCTTTGTTGTGTGAGTTGAAATGAAGTGGGGGCGTCGACTTGGGTGTAATTCTTCATCGCCTGC

TGAACAGGTTGCACTGTTGGCAAGGAGAGCAGTTGGTGTGGATTGGATAGGACTTTTTCCTTGGTCT

ATACGACAATCAATAGCCCGAAGATAGTAGATCAGATGATATGATATATGCTGATTATCTTCATTGG

GCTAGCACAGCACAGCGTTAGCAGACGGTAGCAGTCATGCTTTTCTCACCTCAGTCCATCGGAGATT

GAAGATCGGAGATCCTGTGTGCTACATGCATGAGCTGTTGTAAGGGACAAATTGCAGAACACTGCA

ATGAACTAACTATTAACTAGGAGCTTGAAAGTCAGGAGATCAATGATCAGGAAGAAAAATCATCGG

AATTCCCATGCTATTTGTGTACATATAATAAGATGCACATTTGTTCTGAGCGATAATTTTGCTTTTTAT

ATCTATCCATTTAGGCTAATACCAGTACTACGTACTTCGCATTTCACAGTTCACAGAGTAGTACATAC

GTACAGATAACACAGCATCACAAACCCAGATACCACCACAGACTGCATCACAGTAGCAACATGGAGT

CTGAGCTTTGGGAGTTGATTGAGAGACTTGTTGAATTGCCTGTGAAGAGCCGTATAATTGACTGTCT

GAAATTATACTGTCTTTAATGGGGACTGGAGACTCATCAAATAAAACTTGACTCGCATGTTGAGGAC

CATTGATGCCGTGAGCATGTGTTTATTATGGATATGGACGGATACTATGGCTAAGTAAGAATCTGAT

GTTCCTGTTATTGCCTCTTTCATCATCATACAGTTCGGCGAACCTTGTGCAAAGATAGCCCTGAGATA

AGTGTACGACGGAAACATGTCCCTGAGCGACGGGTATGAAATATTCAGGGTCTTCACAAGTCGCAA

TCCGCAATCCGGCATTTTTCACCATTTGCCGTATCCGGCCTCGGCTCCGTACGTATTCCCACCAAGAA

TCTAACACAACACCAACAAACACCTATAAACTTCACTGCTTCTTCCCCTCCCCTTCTTCATCAGCGCTG
```

```
-continued
CCCCTCCATCCTCTACCTCCCCTACTGCCTATACCACGATCCTCTTCCCTCACACATAACCTCCTCCTC

TCTCTTTCTCCCCTATCTTTTCTTCGGTACGTCTGTTTACTCACCCATCAAGCGGTTTATTGTTGTGTA

CCTATGATCCTTCCCAATTCGATCAAATCAGTTGGTGTCTAACTTCGCACGCAGTCTTTCTGTACAAG

AAGTTGCTCTCCCTTCTGTCTTTCGGCATAACGTCAGCCTCTTGCCCACCCCCACACAACCACATGTA

AGCACATCCTCTAAGCACATCCTCTCCTTTCGTCTACAAACGGAGAAACTATTACGTATACAACAGG

ACAAGGGCTGACTTTAACCTATTCAATCAGAACGGCCCGTTAGA ATGTACGGTCATTTATCTCTCTC

CGCACTTTCCTTGTTTGCAGTGGTGGCCGCTGCTCCATTCCGGGAGTCATGGCTTCAGCCTAGAGATT

CCCCCGTCTCACAGCTGTTCAGACGAAaGCTCCCGATCCCAACTCCAATGGTCAGTACCATCTTCTA

CTATCTCTCAATAAGTAGGACGAGATTTCACTCATATTCCTTTATAGATTACATGAGTTACTATCCAG

GCCCTGGGTCCACTCCGAACGTCAGCACCATTCCCCAAGCTTGGTTGGATAAACTTGCCACAGTGAA

CTTGCCAAATGTTCCAGTAGCTACACCTGATGGTGGTCGTCCTACTTACCCTAATAATGAGGACGAT

GGTGACTCGACAATTTGTTCTTTCACCGATCAATGCCGCGTAGAGGACGATCTGTACTCTCCCCCGG

GTGAGAAGATCTGGGCCGTGAGTGTTATATACTTCTCCATTCATTGTCATCTAGAGATGTGATTAAC

GCGGGTATACAGCTTTCCTTCGACGATGGACCCACAGACGTCAGTCCTGCTCTCTACGACTATCTGG

CTCAGAACAACATATCGTCCTCTGCGACTCATTTCATGATCGGCGGTAATGTTATTACTTCGTATGTC

TCGACCTGCAGCATGTCCCTGCAGGTGTTGTAATATTGACTTTGTGAAATGTAACAGCCCACAGTC

AGTTCTCGTTGCCGTTAAGGCTGGAGGTCACCTTGCCGTCCACACTTGGTCCCATCCTTATAGTGAGT

ATTTGTTAAATTAAAGCACGATTAGTTTTTAAGTCATTTCTTGCAGTGACAACTCTTACCAACGAGC

AAGTCGTTGGAGAGCTCGGCTGGACCATGCAGGCCCTTAGCGATCTCAATGGTGGCCGAATTCCCA

TGTACTGGCGCCCTCCGTATGGAGATGTTGACAACCGTGTCCGAGCTATTGCGAAGGAAGTATTTGG

CTTGGTGACTGTCCTTTGGGATTCGGGTGAGCATCTTGCTTCATGCTGTGGATAAATTGCTAATGGA

TCATAGACACCAATGATTGGGCTATTACCGACGAGCCAGGCCAGTACTCTGTTGCAAGCGTTGAGG

CTTACTTCGACACTTTGGTCACTGGCAATCGAACCCAAGGTCTTTTGCTCTTAGAACATGAGCTGGAT

AACAACACTGTTGAAGTCTTCGAAACGGAGTACCCCAAGGCAGTGGGTAATGGATGGACTGTCAAG

AATGTGGCCGATGCTTTTAACATGGAATGGTACCTGAACTCTGGCAAGGGCAACAACGACGTTGTCA

CAACTATGTCTGTTGCCGGTACCCTGACCACGGCCACGCCAACTAATACTTCTACCTATGTCGCTTCC

TCAACTGCAGCCTCCAGTGCTTCAGTCACGGACTCAGCCGGTGTGTCGATTGCCTCTGCTGCGAGCT

CCGAAGCGTCTTCTTCGTGGGCCATTGCCAACAGGCCTTCTCACTTCGTCATCGCCATCGCGTGCGGC

CTTGCCCTTGCTGCTATAATGGTC TGATAGATGCCATGTGCACTTTTTTGTCGGTCTTTTTAGATCATG

GACTCTCATTCGCATTATATAGGAATCATGGACATATAATTCATTTTTATTGCCATAGACAGTCAAGG

ATTGTTAGATTGTAGCAGTACATTGTTTTTTTCTTTTTTTGTGAATAATGGACAATTTATTTAGTAGTT

GTTTAATTAATCGTCATCAACATTCATTAGCTTTTTCATTTAATAGCACAACAAGGCCGGCAACCAAA

ATGAGTAGAACATGTATACTGTCTTCACAACA
```

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates that exposure of mice to a composition of the present teachings confers immunity to *Cryptococcus* infection in a model system.

In these experiments, illustrated in FIG. 1A, a group of 5 mice were inoculated through nasal inhalation with $10^7$ *Cryptococcus neoformans* cda1Δcda2Δcda3Δ. These mice were challenged with $10^5$ wild type (strain KN99) at day 38 post inoculation. At 70 days post inoculation, 100% of these mice were alive. In contrast, 100% of a control group of 4 mice that had not been inoculated with *Cryptococcus neo-* formans cda1Δcda2Δcda3Δ were dead within 15 days after being challenged with $10^5$ wild type *Cryptococcus neoformans* (strain KN99). These data demonstrate the effectiveness of inhalation exposure to *Cryptococcus neoformans* cda1Δcda2Δcda3Δ for conferring immunity to *Cryptococcus neoformans* infection.

Figure 1B:
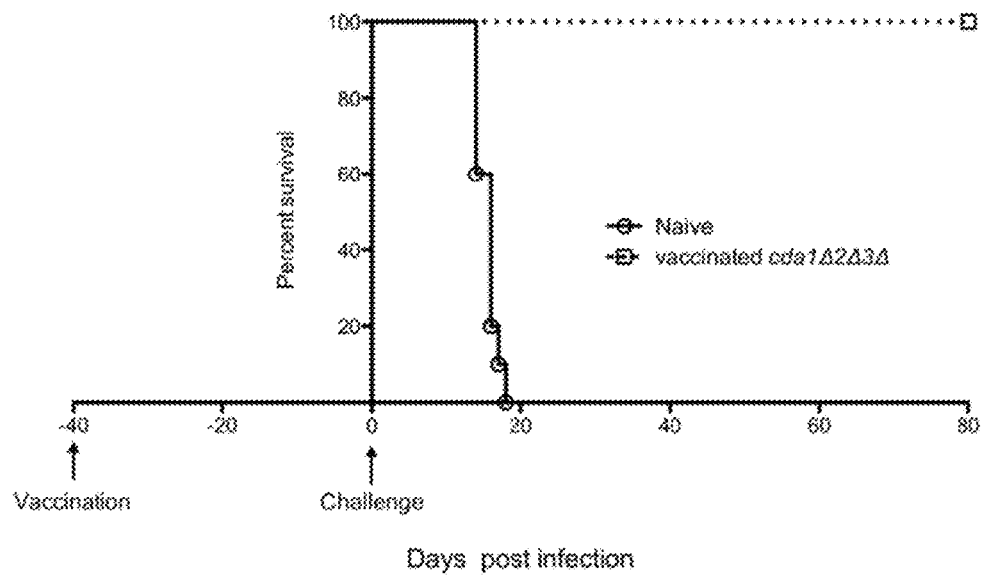

In a second experiment, ten CBA/J mice were vaccinated with $10^7$ of a live preparation of cda1Δ2Δ3Δ cells. After 40 days post vaccination, the vaccinated mice and a group of ten naïve CBA/J mice were challenged with 100,000 of *C. neoformans* cells. FIG. 1B shows that 100% of the vaccinated mice survived to 80 days post infection, while 100% of the naïve mice were dead by 20 days post infection.

Example 2

This example illustrates preparation and use of heat-killed *Cryptococcus* deficient for chitosan production for conferring immunity against *Cryptococcus* infection.

In these experiments, a suspension of *Cryptococcus neoformans* cda1Δcda2Δcda3Δ in phosphate-buffered saline (PBS) is heated to 80° C. for 30 minutes. Test platings on nutrient medium are used to confirm the loss of viability of these *Cryptococcus neoformans* cda1Δcda2Δcda3Δ. Test mice are exposed to these heat-killed fungi as in Example 1. These animals can survive a challenge infection with wild type *Cryptococcus neoformans*. Such experiments can show that heat-killed *Cryptococcus* deficient for chitosan production can be effective for conferring immunity, with efficacy similar to that obtained using live *Cryptococcus neoformans* cda1Δcda2Δcda3Δ.

Example 3

This example illustrates that inactivated *Cryptococcus neoformans* deficient for chitosan production is effective as a vaccine against *C. neoformans* infection in a mouse model system.

Figure 2A:
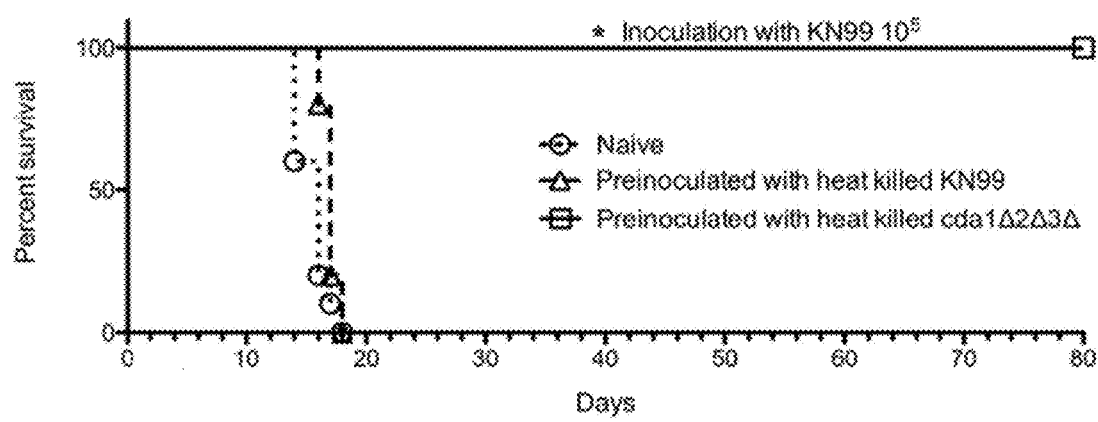
FIG. 2A-B illustrates that mice exposed to heat-killed *Cryptococcus neoformans* cda1Δcda2Δcda3Δ survive wild type *Cryptococcus neoformans* infection.

In these experiments, *C. neoformans* fungi (strain KN99), and *C. neoformans* cda1Δcda2Δcda3Δ subjected to heat-killing. For each strain, heating was applied until samples formed no colonies on standard nutrient plates. 5 mice were inoculated by nasal administration with $10^5$ heat-killed KN99, and 5 mice were inoculated by nasal administration with $10^7$ heat-killed *C. neoformans* cda1Δcda2Δcda3Δ. The inoculated mice and 10 naïve control mice were challenged with $10^5$ wild type *C. neoformans* KN99 40 days after inoculation. As shown in FIG. 2A, no naïve mice or mice treated with heat-killed KN99 survived more than 18 days after exposure to wild type *C. neoformans*. In contrast, 100% of mice inoculated with heat-killed *C. neoformans* cda1Δcda2Δcda3Δ survived more than 70 days after exposure to wild type *C. neoformans*.

Figure 2B:
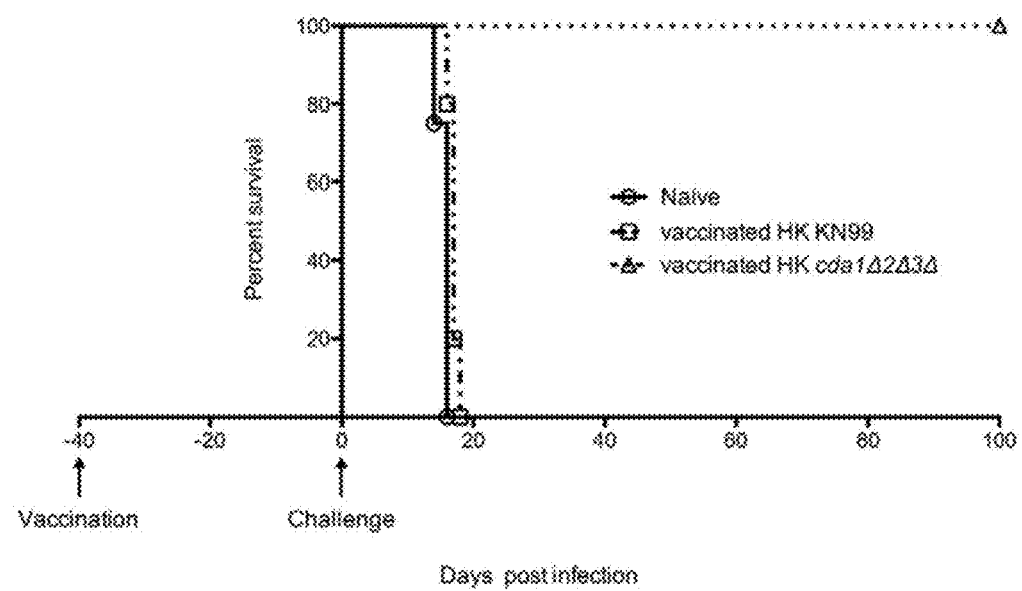

In a second experiment, ten CBA/J mice were vaccinated with $10^7$ of a heat-killed preparation of wild type (KN99) cells and ten CBA/J mice were vaccinated with $10^7$ of a heat-killed preparation of cda1Δ2Δ3Δ cells. Ten phosphate buffered saline (PBS) vaccinated mice served as control. After 40 days post vaccination, all mice were challenged with 100,000 of *C. neoformans* cells. FIG. 2B shows that 100% of mice vaccinated with heat attenuated *C. neoformans* cda1Δcda2Δcda3Δ live to 100 days post infection. In contrast, no mice vaccinated with PBS or heat-killed wild type *C. neoformans* cells live to 20 days post infection.

These data demonstrate that heat-killed *C. neoformans* cda1Δcda2Δcda3Δ can confer immunity to *C. neoformans* infection.

Example 4

This example illustrates vaccination of a human subject against infection by *Cryptococcus neoformans*.

In this example, *Cryptococcus neoformans* cda1Δcda2Δcda3Δ is grown by standard protocols. The fungi are pelleted and resuspended in phosphate-buffered saline 3 times. Following the final resuspension, the *Cryptococcus neoformans* cda1Δcda2Δcda3Δ suspension is administered to a human subject via a nasal spray. The subject does not subsequently develop a *Cryptococcus neoformans* infection for at least one year.

Example 5

This example illustrates vaccination of an animal subject against infection by *Cryptococcus gattii*.

In this example, *Cryptococcus gattii* cda1Δcda2Δcda3Δ is grown by standard protocols. The fungi are pelleted and resuspended in phosphate-buffered saline 3 times. Following the final resuspension, the *Cryptococcus gattii* cda1Δcda2Δcda3Δ suspension is administered to a dog subject via a nasal spray. The dog does not subsequently develop a *Cryptococcus gattii* infection for at least one year.

Example 6

This example illustrate conferral of immunity to *C. neoformans* by administration of *C. neoformans* cda1Δ.

Figure 3:
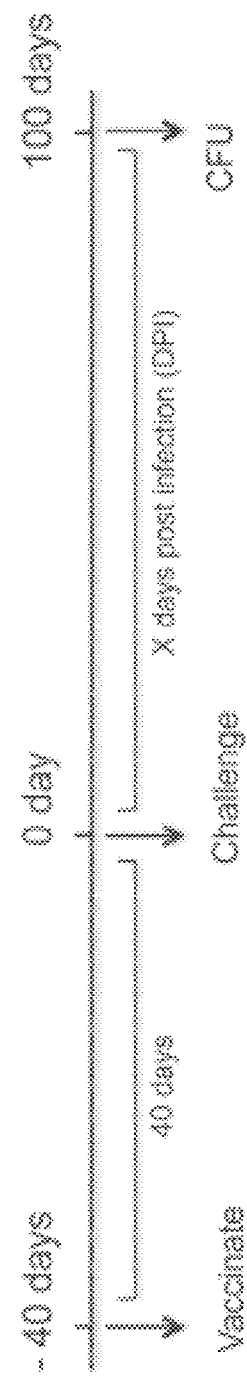
FIG. 3 illustrates an experimental protocol for testing *Cryptococcus neoformans* cda1Δ as a vaccine.

In these experiments, as illustrated in FIG. 3, 4 CBA/J female mice (4-6 weeks of age) were subjected to an immunization schedule using nasal administration of a live preparation of $10^6$ *Cryptococcus neoformans* cda1Δ. At −54 days, the mice were placed in laboratory housing. At −40 days, the mice were each vaccinated with $10^5$ *C. neoformans* cda1Δ. At day 0 (40 days post vaccination), the mice were exposed to $10^5$ KN99 (wild-type *C. neoformans*). As a control, 10 naïve mice were subjected to the same schedule but were not vaccinated before the challenge with KN99. Weight of the mice was monitored; animals were euthanized when weight fell below 75% of starting weight.

Figure 4:
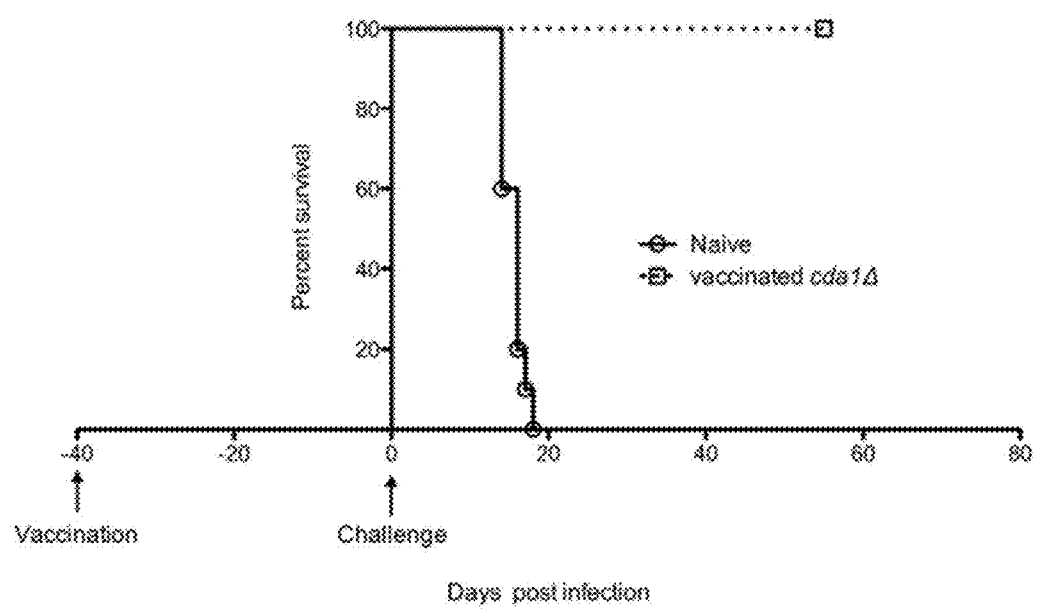
FIG. 4 illustrates a survival curve of a cda1Δ pilot experiment described in FIG. 3.

The results of the challenge are shown in FIG. 4. The data indicate that the 100% of naïve mice were dead in less than 20 days after exposure to *C. neoformans* KN99, but that 100% of vaccinated mice remained alive more than 50 days after exposure to *C. neoformans* KN99.

These data demonstrate effectiveness of nasal administration of *C. neoformans* cda1Δ for vaccination against *C. neoformans* infection.

Example 7

This example illustrates conferral of immunity to *C. gattii* by administration of *C. neoformans* cda1Δcda2Δcda3Δ.

Figure 5:
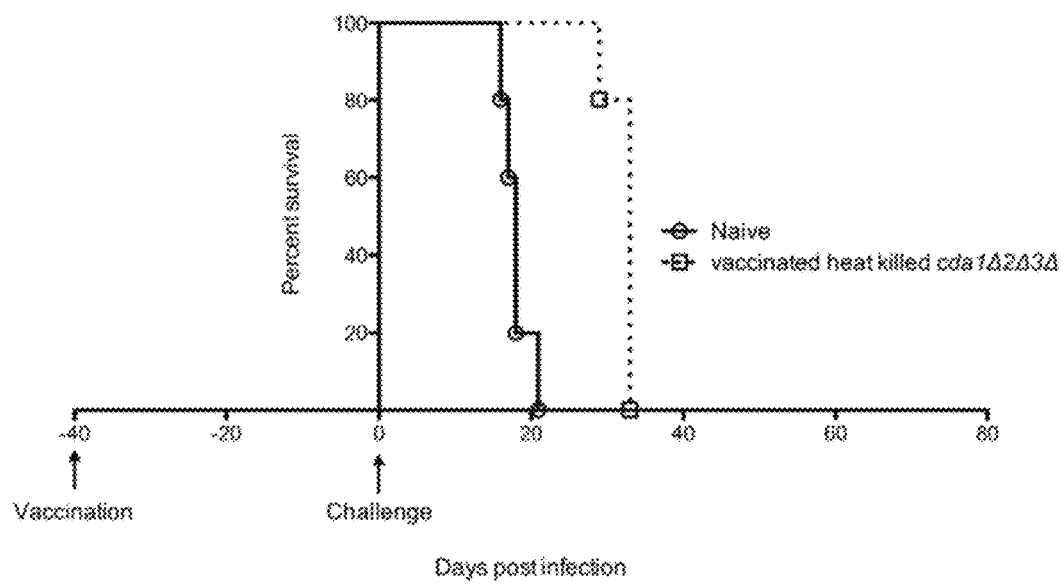
FIG. 5 illustrates a survival curve of vaccinated mice immunized with *C. neoformans* cda1Δ challenged with R265 (*C. gattii*).
Figure 6:
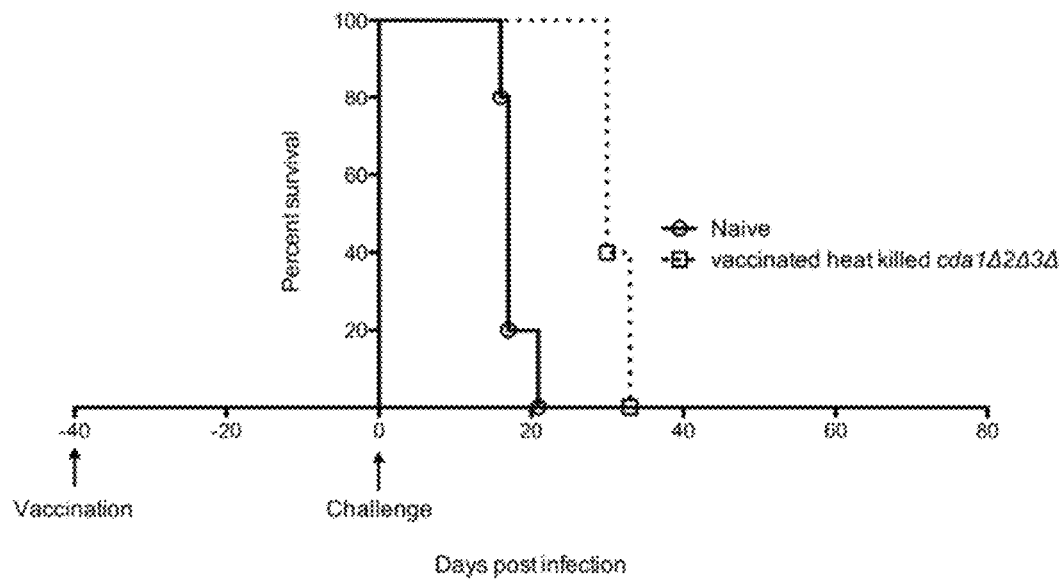
FIG. 6 illustrates a survival curve of vaccinated mice immunized with *C. neoformans* cda1Δ challenged with WM226 (*C. gattii*).
Figure 7:
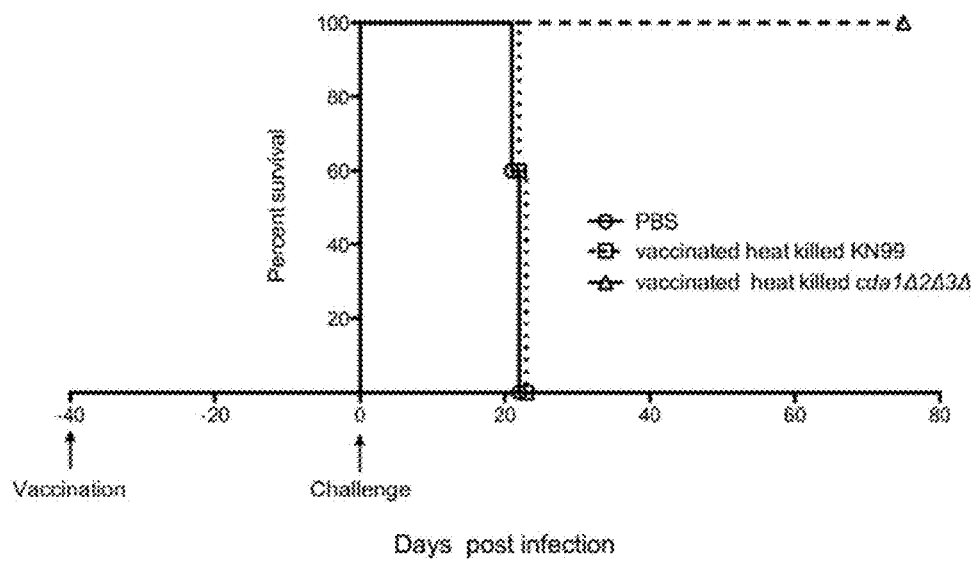
FIG. 7 illustrates that 129 mice immunized with *Cryptococcus neoformans* cda1Δcda2Δcda3Δ survive when challenged with *C. neoformans*.
Figure 8:
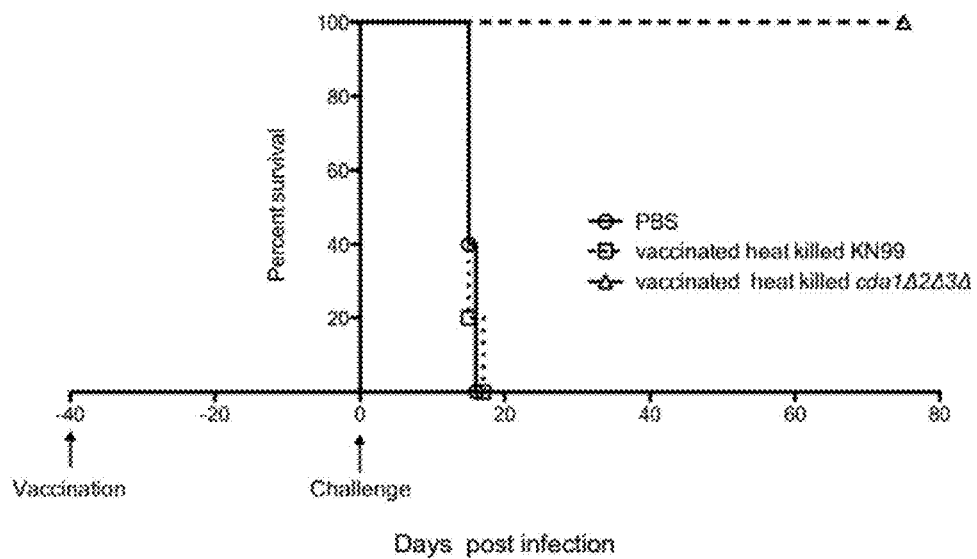
FIG. 8 illustrates that A/J mice immunized with *Cryptococcus neoformans* cda1Δcda2Δcda3Δ survive when challenged with *C. neoformans*.
Figure 9:
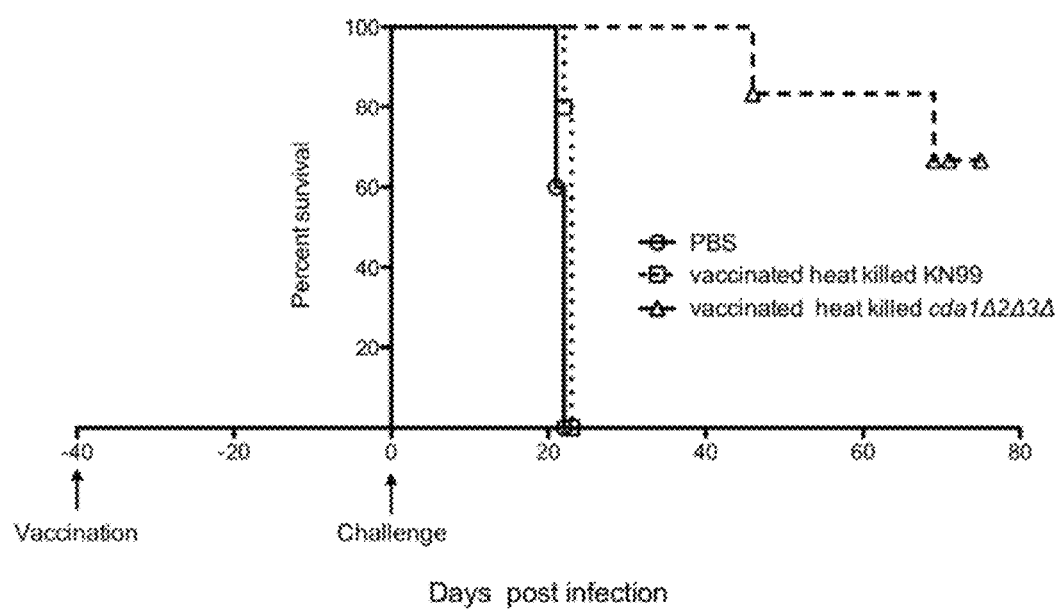
FIG. 9 illustrates that 129 mice immunized with *Cryptococcus neoformans* cda1Δcda2Δcda3Δ survive when challenged with *C. neoformans*.
Figure 10:
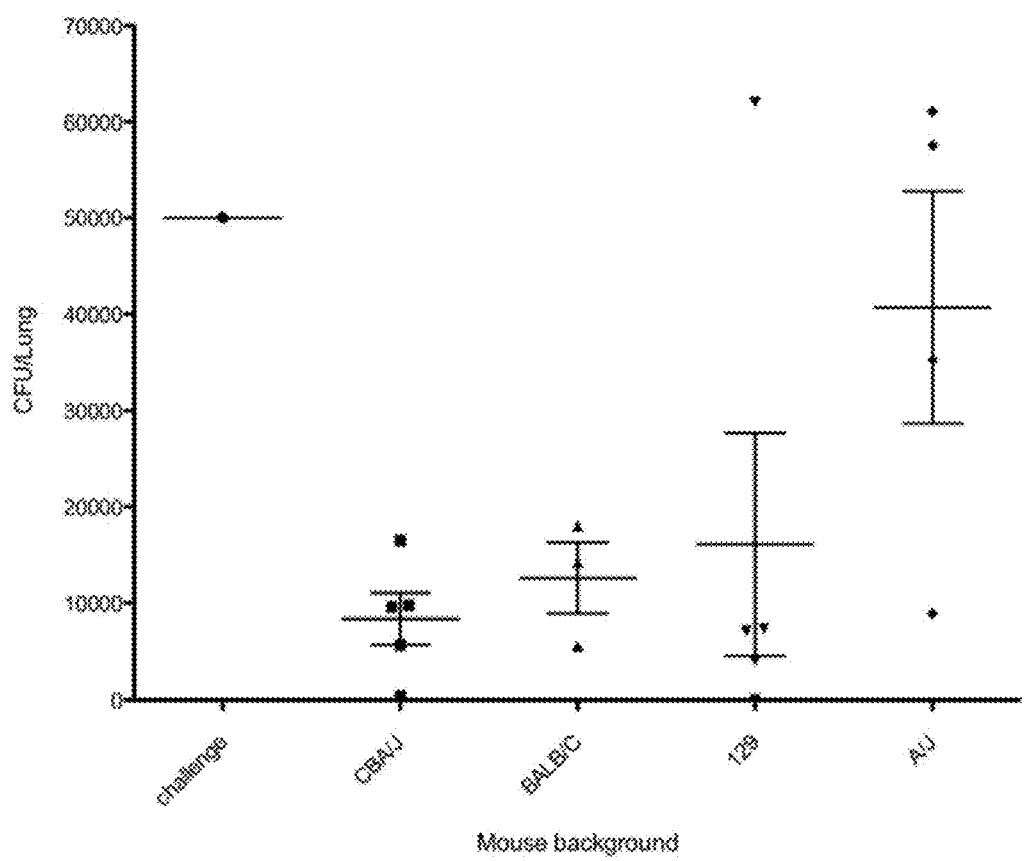
FIG. 10 illustrates fungal burden for surviving mice of different strains after the conclusion of survival experiments.
Figure 11:
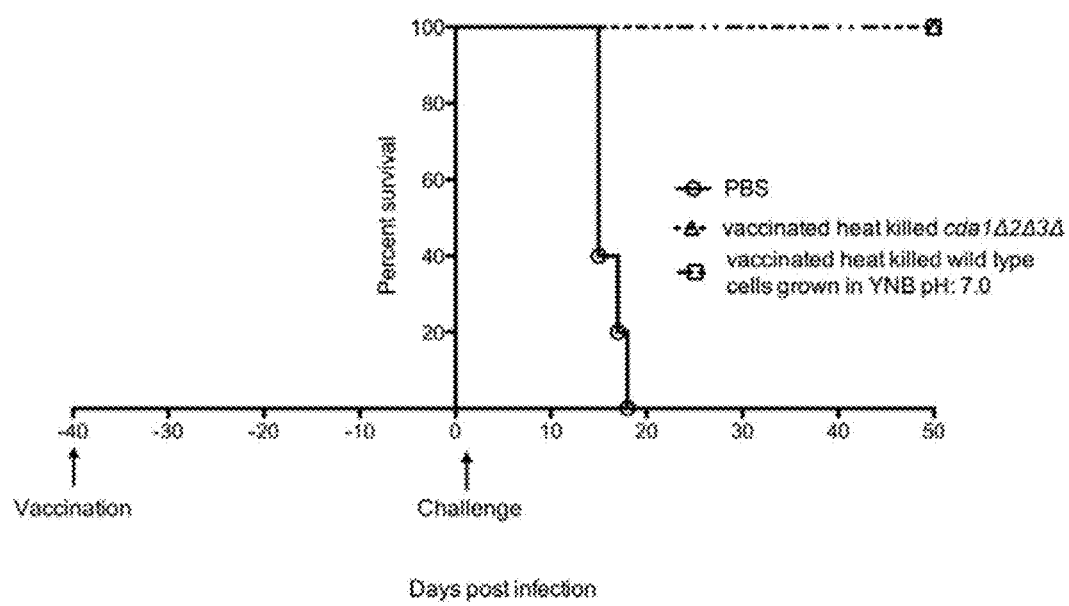
FIG. 11 illustrates that CBA/J mice immunized with heat-killed wild type cells grown in YNB pH 7.0 medium buffered to pH 7.0 survive when challenged with *C. neoformans*.
Figure 12:
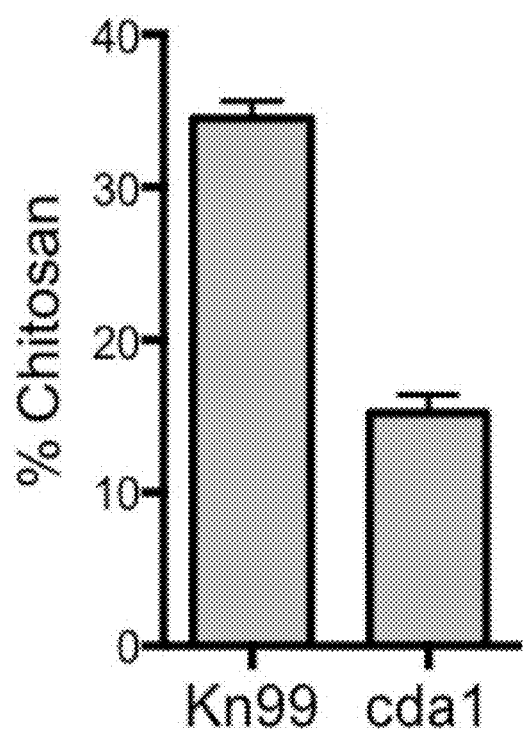
FIG. 12 illustrates chitosan levels present in mouse lungs when inoculated with wild type or cda1Δ *C. neoformans*.
Figure 13:
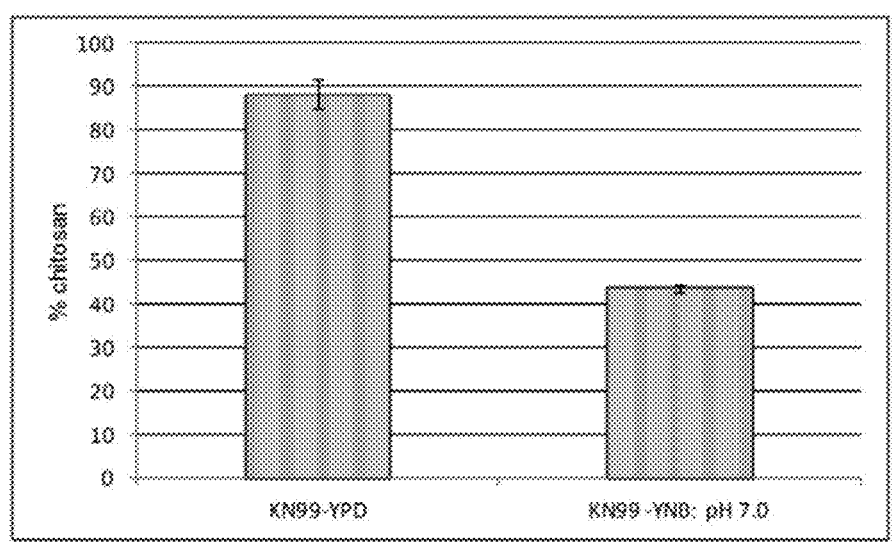
FIG. 13 illustrates chitosan levels present in wild type *C. neoformans* cells when grown on YPD medium or YNB medium buffered to pH 7.0.

In these experiments, 10 CBA/J mice were vaccinated with $10^7$ of a heat-killed preparation of *C. neoformans* cda1Δcda2Δcda3Δ by nasal administration, while an additional 5 naïve mice were kept as controls. The vaccinated mice and the naïve control mice were exposed to *Cryptococcus gattii* strain R265. As illustrated in FIG. 5, all of the naïve mice were dead by 21 days after exposure to *C. gattii* R265. In contrast, 100% of mice inoculated with *C. neoformans* cda1Δcda2Δcda3Δ were alive at 21 days after exposure to *C. gattii* R265. Survival extended to over 30 days in the vaccinated mice.

These data survival at least partial protection against *C. gattii* infection by administration of *C. neoformans* deficient for chitin deacetylase.

Example 8

This example illustrates conferral of immunity to *C. gattii* by administration of *C. neoformans* cda1Δcda2Δcda3Δ.

In these experiments, 10 CBA/J mice were vaccinated with $10^7$ of a heat-killed preparation of *C. neoformans* cda1Δcda2Δcda3Δ by nasal administration, while an additional 5 naïve mice were kept as controls. The vaccinated mice and the naïve control mice were exposed to *Cryptococcus gattii* strain WM266 40 days post vaccination. As illustrated in FIG. 6, all of the naïve mice were dead by 21 days after exposure to *C. gattii* WM266. In contrast, 100% of mice inoculated with *C. neoformans* cda1Δcda2Δcda3Δ were alive at 21 days after exposure to *C. gattii* WM266. Survival extended to over 30 days in the vaccinated mice.

These data demonstrate at least partial protection against *C. gattii* infection by administration of *C. neoformans* deleted for chitin deacetylases genes.

Example 9

This example illustrates the induction of protective response to *C. neoformans* infection in 129 mice after vaccination with heat-killed cda1Δ2Δ3Δ.

In these experiments, five 129 mice were vaccinated with $10^7$ heat-killed preparation of wild type (KN99) and five 129 mice were vaccinated with $10^7$ heat-killed preparation of cda1Δ2Δ3Δ cells by nasal administration. Phosphate buffered saline (PBS) vaccinated mice served as control. After 40 days post vaccination, mice were challenged with 50,000 of *C. neoformans* cells. FIG. 7 illustrates the survival of 129 mice vaccinated with heat-killed cda1Δ2Δ3Δ. As with other mouse strains, 100% of the mice vaccinated with cda1Δ2Δ3Δ survived for 80 days post challenge, while controls vaccinated with wild type *Cryptococcus* or PBS died about 20 days after *C. neoformans* challenge.

Example 10

This example illustrates the induction of protective response to *C. neoformans* infection in A/J mice after vaccination with heat-killed cda1Δ2Δ3Δ cells by nasal administration.

In these experiments, five A/J mice were vaccinated with $10^7$ of a heat-killed preparation of wild type (KN99) and five A/J mice were vaccinated with $10^7$ of a heat-killed preparation of cda1Δ2Δ3Δ cells by nasal administration. Five phosphate buffered saline (PBS) vaccinated mice served as a control. After 40 days post vaccination, all mice were challenged with 50,000 of *C. neoformans* cells. FIG. 8 illustrates that 100% of mice vaccinated with heat-killed cda1Δ2Δ3Δ cells survived for 80 days after challenge with *C. neoformans* cells. In contrast, controls vaccinated with PBS or heat-killed KN99 died within 20 days of challenge with *C. neoformans* cells.

Example 11

This example illustrates the induction of protective response to *C. neoformans* infection in BALB/c mice after vaccination with heat-killed cda1Δ2Δ3Δ.

In these experiments, five BALB/c mice were vaccinated with $10^7$ of a heat-killed preparation of wild type (KN99) and five BALB/c mice were vaccinated with $10^7$ of a heat-killed preparation of cda1Δ2Δ3Δ cells by nasal administration. Five phosphate buffered saline (PBS) vaccinated mice served as a control. After 40 days post vaccination, mice were challenged with 50,000 of *C. neoformans* cells. FIG. 9 illustrates that 100% of mice vaccinated with cda1Δ2Δ3Δ cells lived at least 40 days post challenge, with over 60% surviving to 80 days. In contrast, 100% of mice vaccinated with PBS or heat-killed wild type cells died shortly after 20 days post challenge.

Example 12

This example illustrates the fungal burden in the lungs of cda1Δ2Δ3Δ vaccinated mice that exhibited complete protection when challenged with *Cryptococcus neoformans*.

In these experiments, several strains of mice were vaccinated by nasal administration with a preparation of $10^7$ heat-killed cda1Δ2Δ3Δ cells. After 40 days post vaccination, the mice were challenged with 50,000 of wild type (KN99) *C. neoformans* cells in experiments discussed infra. At the conclusion of each of these experiments, surviving mice were sacrificed. Lungs were homogenized and plated onto fungal media to determine the CFU of *C. neoformans* still present in the lungs. FIG. 10 illustrates the fungal burden for each strain.

Example 13

This example illustrates the induction of a protective response to *C. neoformans* infection in CBA/J mice after vaccination with a heat-killed preparation of wild type cells grown in Yeast Nitrogen Base medium (YNB) buffered to pH 7.0.

In these experiments, five CBA/J mice were vaccinated by nasal administration with a preparation of $10^7$ heat-killed of wild type cells grown in Yeast Nitrogen Base medium buffered to pH 7.0 with 50 mM 3-(N-morpholino) propanesulfonic acid (MOPS) and five CBA/J mice were vaccinated with $10^7$ of a heat-killed preparation of cda1Δ2Δ3Δ cells. Five phosphate buffered saline (PBS) vaccinated mice served as control. After 40 days post vaccination, mice were challenged with 50,000 of *C. neoformans* cells. FIG. 11 illustrates that mice vaccinated with heat-killed wild type cells that were grown in YNB medium pH 7.0 survive to 50 days post challenge at the same rate as cda1Δ2Δ3Δ vaccinated mice. Mice vaccinated with PBS in this experiment did not survive to 20 days post challenge.

Example 14

This example illustrates the relative chitosan levels of different *C. neoformans* strains isolated from mouse lungs.

Wild type (KN99) and cda1Δ were inoculated (100,000 cells) to mouse lungs by nasal inhalation. The lungs were excised 16 days post infection. *C. neoformans* cells were isolated from the lung homogenate and used for chitosan determination. FIG. 12 illustrates the chitosan levels present in lungs inoculated with each strain; cda1Δ chitosan levels were 50% that of KN99 wild type chitosan levels.

Wild type cells (KN99) were grown in Yeast Extract Peptone Dextrose (YPD) or Yeast Nitrogen Base (YNB) buffered to pH: 7.0 with 50 mM 3-(N-morpholino) propanesulfonic acid (MOPS). Equal number of cells were subjected to chitosan measurements. FIG. 13 illustrates that the level of chitosan in KN99 cells grown in YNB pH 7.0 medium is less than 50% that of the level of KN99 cells grown in YPD medium, a similar reduction to that between wild type cells and cda1Δ cells isolated from mouse lungs.

All references cited herein are incorporated by reference, each in its entirety.

What is claimed is:

1. A method of inducing immunity against a *Cryptococcus* fungus infection wherein the *Cryptococcus* is selected from the group consisting of *Cryptocoecus neoformans* and *Cryptococcus gattii*, comprising administering to a subject by inhalation an immunity-inducing amount of a composition comprising a *Cryptococcus* fungus deficient for chitosan, wherein the *Cryptococcus* fungus deficient for chitosan is selected from the group consisting of a *Cryptococcus neoformans* fungus deficient for chitosan and a *Cryptococcus gattii* fungus deficient for chitosan, and wherein the *Cryptococcus* fungus deficient for chitosan comprises no more than 60% chitosan level compared to wild type grown on yeast extract peptone dextrose (YPD) and wherein the *Cryptococcus* fungus deficient for chitosan is a heat-inactivated cdaIΔcda2Δcda3Δ *Cryptococcus* fungus deficient for chitosan.

2. A method of inducting immunity against a *Cryptococcus* fungus infection in accordance with claim 1, wherein the *Cryptococcus* fungus deficient for chitosan comprises no more than 50% chitosan level compared to wild type *grown* on yeast extract peptone dextrose (YPD).

3. A method of inducing immunity against a *Cryptococcus* fungus infection in accordance with claim 1, wherein the *Cryptococcus* fungus deficient for chitosan is a *Cryptococcus neoformans* fungus deficient for chitosan.

4. A method of inducing immunity against a *Cryptococcus* fungus infection in accordance with claim 1, wherein the *Cryptococcus* fungus deficient for chitosan is a *Cryptococcus gattii* fungus deficient for chitosan.

5. A method of inducing immunity against a *Cryptococcus* fungus infection in accordance with claim 1, wherein the administering by inhalation comprises nasal inhalation.

6. A method of inducing immunity against a *Cryptococcus* fungus infection in accordance with claim 5, wherein the nasal inhalation is selected from the group consisting of inhaling a nose drop formulation and inhaling a nasal spray formulation.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Cryptococcus neoformans

<400> SEQUENCE: 1
ggccctctac tctaccttcg                                                 20

<210> SEQ ID NO 2
<211> LENGTH: 21
<212> TYPE: DNA
<213> ORGANISM: Cryptococcus neoformans

<400> SEQUENCE: 2
gccgcctcta acacttcttc c                                               21

<210> SEQ ID NO 3
<211> LENGTH: 2544
<212> TYPE: DNA
<213> ORGANISM: Cryptococcus neoformans

<400> SEQUENCE: 3
gccgaacagc gcaggtcagg gagagcattt ctagcgtgcc ttggtagatc gttatcgcga      60
tttactttcc aggccctggg cgcttccagc catcagccaa aggataaaag cgcgtgccct     120
cttcttttca tcattaactt ttatcctcct cagcacccac gctctgtgat tccatctctt     180
cctcctcgca ttcaagcagc ctcttcattt ctttcctccg tcccggtgag tgcgacgccc     240
gccgctgcca ttcccacacg atgacttgag acgcgtcttc ccgctatagc cgacgcccct     300
tttcgttttc ttggcgtttt gtcacattgc cacattgagc agcacagctt acttgtcagc     360
agcaaaaatc caacttcaaa cagctcttca gcatcaactc tatcactctt tcatctcttg     420
tcaacttctc ttccttctcg ctccaaaagc ggaatttcgc catgtttaca ttcgctgcct     480
tctctgctct tctaatttcc ctcgctggtg tggtggcgca gactacaggc acatcggttg     540
acagtagcat cttaactaag actgctgact ctaccggtcc ctctggtttc tccattccgt     600
gagtactctc gacttttccg tcaacctcca gtctcgccac aggccatagc gaacaatgag     660
ccaagcgccc acgcgaaccg tgcccatcat tatcctccca ctaattcctt taaccaaacg     720
tagcttttag aggccaaatg ctgacaagtg cgttttttagt gctttgagcg agctcacgtc     780
tggtgccccc actgactcta ctgtggccct ctactctacc ttcgcggccg gtgccacacc     840
taccgtttct ggtgcccctg tcctccctac cagtgccctc accatcgccg attatccagc     900
tttagatgtc acccctccta ccaactcctc tttggttaag gactggatgg ccaaggtgag     960
ttgtgtttga gtccgaaaag gcaccagaag agctaacagt tggattagat cgacttgtcc    1020
aaggtgccca gttataatgt gacaacgggc gattgttcta ctgacgcggc tgctatcagc    1080
gacggtcgat gctggtggac ttgtggtggt tgcactcggg aaaccgacat tgtcgagtgt    1140
cctgacaaga atgtttgggg tctctcttac gatgatgggc cttctccctt caccctctc    1200 ctaattgatt accttcagga gaagaacatc aagaccacct tcttcgttgt cggctctcgt    1260
gtcctttctc gacccgagat gctccaaacc gaatacatgt ctgacaccca gatctctatc    1320
cacacttggt ctcacccccgc acttactact cttaccaacg aggaaattgt tgccgagctt    1380
```

```
ggttggacaa tgaaggtcat caaggacacc cttggcgtca ccccaaacac tttccgaccc      1440
ccttatggtg acattgatga ccgtgttcga gctattgctg ctcagatggg cttgacccct      1500
gttatctgga cttcttacac tgatggctca accactgtta actttgacac tgtaggctta      1560
tcttgacttt cgcaataatc ttactaacga aatgacagaa cgactggcac atcagtggtg      1620
gtaccgccac cggcgcttct tcttatgaga cctttgagaa gattctcacc gaatacgccc      1680
caaagttgga cactggtttc atcactcttg agcacgacag taagtcttgt ctatccgtct      1740
tgcaataata atcctgacgt ataccttac agtctaccag cagagtgttg accttgctgt       1800
tggttacatt ttgccccaag ttctcgccaa cggtacctat cagctcaaat ccatcatcaa      1860
ctgtttgggc aaggacagta agttgcctcc gctaatcaga aaaggttgtg ggctaagatg      1920
atacacagcc tccgaagcat acattgagac ttcatccaac cagactacta ctcagatcac      1980
tgcagccacc ggctcccagt ctaccttctt ccagcccatt gttggcactg ctaccggtgc      2040
tgaagtctct gcaccttctg aggccactgg cagcactgcc gctggctctg ctgcctccac      2100
cactagtggt tctggcgcca gcgcttctac aggcgccgcc tctaacactt cttccagcgg      2160
gtctggtcga tcagccacca tgggtggtgc cctcattgct cttgccgctg ttgcggttgg      2220
tatggtatat gtcgcctaag tatttcaagg ctttcaatgt aacgatggat ggggatgggt      2280
ggtgggggg gagggaagtg tgtctaatgg ggctatactt gggctatact ttgcctcaaa      2340
tccatcaagt attaatagct gaaccatctt tcgttgaacc gtctttcatt gtgaaccatt      2400
tgtctttttg atctttcaaa gtttgatcca ttatgaatat catggacatt ttgaacgttt      2460
tgaacatcca tgtactttc attcgatcga tctgaacgtg ttgttgtgca tacctcgcga       2520
acaagctttc aatggatggc ttca                                             2544

<210> SEQ ID NO 4
<211> LENGTH: 2545
<212> TYPE: DNA
<213> ORGANISM: Cryptococcus neoformans

<400> SEQUENCE: 4
gccgaacagc gcaggtcagg gagagcattt ctagcgtgcc ttggtagatc gttatcgcga       60
tttactttcc aggccctggg cgcttccagc catcagccaa aggataaaag cgcgtgccct      120
cttcttttca tcattaactt ttatcctcct cagcacccac gctctgtgat tccatctctt      180
cctcctcgca ttcaagcagc ctcttcattt cttttcctcc tcccggtgag tgcgacgccc      240
gccgctgcca ttcccacacg atgacttgag acgcgtcttc ccgctatagc cgacgccct       300
tttcgttttc ttggcgtttt gtcacattgc cacattgagc agcacagctt acttgtcagc      360
agcaaaaatc caacttcaaa cagctcttca gcatcaactc tatcactctt tcatctcttg      420
tcaacttctc ttccttctcg ctccaaaagc ggaatttcgc catgtttaca ttcgctgcct      480
tctctgctct ctaatttcc ctcgctggtg tggtggcgca gactacaggc acatcggttg       540
acagtagcat cttaactaag actgctgact ctaccggtcc ctctggtttc tccattccgt      600
gagtactctc gacttttccg tcaacctcca gtctcgccac aggccatagc gaacaatgag      660
ccaagcgccc acgcgaaccg tgcccatcat tatcctccca ctaattcctt taaccaaacg      720
tagcttttag aggccaaatg ctgacaagtg cgttttagt gctttgagcg agctcacgtc       780
tggtgccccc actgactcta ctgtggccct ctactctacc ttcgcggccg gtgccacacc      840
taccgtttct ggtgccctg tcctccctac cagtgccctc accatcgccg attatccagc       900
tttagatgtc accctcta ccaactcctc tttggttaag gactggatgg ccaaggtgag        960
```

```
ttgtgtttga gtccgaaaag gcaccagaag agctaacagt tggattagat cgacttgtcc    1020
aaggtgccca gttataatgt gacaacgggc gattgttcta ctgacgcggc tgctatcagc    1080
gacggtcgat gctggtggac ttgtggtggt tgcactcggg aaaccgacat tgtcgagtgt    1140
cctgacaaga atgtttgggg tctctcttac aacgatgggc cttctccctt cacccctctc    1200
ctaattgatt accttcagga gaagaacatc aagaccacct tcttcgttgt cggctctcgt    1260
gtcctttctc gacccgagat gctccaaacc gaatacatgt ctggacacca gatctctatc    1320
cacacttggt ctcaccccgc acttactact cttaccaacg aggaaattgt tgccgagctt    1380
ggttggacaa tgaaggtcat caaggacacc cttggcgtca ccccaaacac tttcgctccc    1440
ccttatggtg acattgatga ccgtgttcga gctattgctg ctcagatggg cttgacccct    1500
gttatctgga cttcttacac tgatggctca accactgtta actttgacac tgtaggctta    1560
tcttgacttt cgcaataatc ttactaacga aatgacagaa caactggcac atcagtggtg    1620
gtaccgccac cggcgcttct tcttatgaga ccttttgagaa gattctcacc gaatacgccc    1680
caaagttgga cactggtttc atcactcttg agcacgacag taagtcttgt ctatccgtct    1740
tgcaataata atcctgacgt ataccttgtac agtctaccag cagagtgttg accttgctgt    1800
tggttacatt ttgccccaag ttctcgccaa cggtacctat cagctcaaat ccatcatcaa    1860
ctgtttgggc aaggacagta agttgcctcc gctaatcaga aaaggttgtg ggctaagatg    1920
atacacagcc tccgaagcat acattgagac ttcatccaac cagactacta ctcagatcac    1980
tgcagccacc ggctcccagt ctaccttctt ccagcccatt gttggcactg ctaccggtgc    2040
tgaagtctct gcaccttctg aggccactgg cagcactgcc gctggctctg ctgcctccac    2100
cactagtggt tctggcgcca gcgcttctac aggcgccgcc tctaacactt cttccagcgg    2160
gtctggtcga tcagccacca tgggtggtgc cctcattgct cttgccgctg ttgcggttgg    2220
tatggtatat gtcgcctaag tatttcaagg cttcaatgt aacgatggat ggggatgggt    2280 ggtgggggggg gagggaagtg tgtctaatgg ggctatactt gggctatact ttgcctcaaa    2340
tccatcaagt attaatagct gaaccatctt tcgttgaacc gtctttcatt gtgaaccatt    2400 tgtcttttg atctttcaaa gtttgatcca ttatgaatat catggacatt ttgaacgttt    2460
tgaacatcca tgtactttc attcgatcga tctgaacgtg ttgttgtgca tacctcgcga    2520
acaagctttc aatggatggc ttcac    2545
```

<210> SEQ ID NO 5
<211> LENGTH: 2580
<212> TYPE: DNA
<213> ORGANISM: Cryptococcus neoformans

<400> SEQUENCE: 5

```
ggaacaataa caaagcacaa cgcgacaaaa gccgaacagc gcaggtcagg gagagcattt      60
ctagcgtgcc ttggtagatc gttatcgcga tttactttcc aggccctggg cgcttccagc     120
catcagccaa aggataaaag cgcgtgccct cttcttttca tcattaactt ttatcctcct     180
cagcacccac gctctgtgat tccatctctt cctcctcgca ttcaagcagc tcttcatttt     240
ctttcctccg tcccggtgag tgcgacgccc gccgctgcca ttcccacacg atgacttgag     300
acgcgtcttc ccgctatagc cgacgcccct tttcgttttc ttggcgtttt gtcacattgc     360
cacattgagc agcacagctt acttgtcagc agcaaaaatc caacttcaaa cagctcttca     420
gcatcaactc tatcactctt tcatctcttg tcaacttctc ttccttctcg ctccaaaagc     480
ggaatttcgc catgtttaca ttcgctgcct tctctgctct tctaatttcc ctcgctggtg     540
```

```
tggtggcgca gactacaggc acatcggttg acagtagcat cttaactaag actgctgact    600
ctaccggtcc ctctggtttc tccattccgt gagtactctc gacttttccg tcaacctcca    660
gtctcgccac aggccatagc gaacaatgag ccaagcgccc acgcgaaccg tgcccatcat    720
tatcctccca ctaattcctt taaccaaacg tagcttttag aggccaaatg ctgacaagtg    780
cgttttagt gctttgagcg agctcacgtc tggtgccccc actgactcta ctgtggccct     840
ctactctacc ttcgcggccg gtgccacacc taccgtttct ggtgccctg tcctccctac      900
cagtgccctc accatcgccg attatccagc tttagatgtc acccctccta ccaactcctc    960
tttggttaag gactggatgg ccaaggtgag ttgtgtttga gtccgaaaag gcaccagaag    1020
agctaacagt tggattagat cgacttgtcc aaggtgccca gttataatgt gacaacgggc    1080
gattgttcta ctgacgcggc tgctatcagc gacggtcgat gctggtggac ttgtggtggt    1140
tgcactcggg aaaccgacat tgtcgagtgt cctgacaaga atgtttgggg tctctcttac    1200
gataacgggc cttctcccct cacccctctc ctaattgatt accttcagga gaagaacatc    1260
aagaccacct tcttcgttgt cggctctcgt gtcctttctc gacccgagat gctccaaacc    1320
gaatacatgt ctggacacca gatctctatc gccacttggt ctgccccgc acttactact     1380
cttaccaacg aggaaattgt tgccgagctt ggttggacaa tgaaggtcat caaggacacc    1440
cttggcgtca ccccaaacac tttcgctccc ccttatggtg acattgatga ccgtgttcga    1500
gctattgctg ctcagatggg cttgacccct gttatctgga cttcttacac tgatggctca    1560
accactgtta actttgacac tgtaggctta tcttgacttt cgcaataatc ttactaacga    1620
aatgacagaa caactggcac atcagtggtg gtaccgccac cggcgcttct tcttatgaga    1680
cctttgagaa gattctcacc gaatacgccc caaagttgga cactggtttc atcactcttg    1740
agcacgacag taagtcttgt ctatccgtct tgcaataata atcctgacgt ataccttac    1800
agtctaccag cagagtgttg accttgctgt tggttacatt ttgccccaag ttctcgccaa    1860
cggtacctat cagctcaaat ccatcatcaa ctgtttgggc aaggacagta agttgcctcc    1920
gctaatcaga aaaggttgtg ggctaagatg atacacagcc tccgaagcat acattgagac    1980
ttcatccaac cagactacta ctcagatcac tgcagccacc ggctcccagt ctaccttctt    2040
ccagcccatt gttggcactg ctaccggtgc tgaagtctct gcaccttctg aggccactgg    2100
cagcactgcc gctggctctg ctgcctccac cactagtggt tctggcgcca gcgcttctac    2160
aggcgccgcc tctaacactt cttccagcgg gtctggtcga tcagccacca tgggtggtgc    2220
cctcattgct cttgccgctg ttgcggttgg tatggtatat gtcgcctaag tatttcaagg    2280
cttttcaatgt aacgatggat ggggatgggt ggtgggggg gagggaagtg tgtctaatgg    2340
ggctatactt gggctatact ttgcctcaaa tccatcaagt attaatagct gaaccatctt    2400
tcgttgaacc gtctttcatt gtgaaccatt tgtctttttg atctttcaaa gtttgatcca    2460
ttatgaatat catggacatt ttgaacgttt tgaacatcca tgtactttc attcgatcga     2520
tctgaacgtg ttgttgtgca tacctcgcga acaagctttc aatggatggc ttcacagatc    2580
```

<210> SEQ ID NO 6
<211> LENGTH: 2104
<212> TYPE: DNA
<213> ORGANISM: Cryptococcus neoformans

<400> SEQUENCE: 6

```
gaaaatcaca gcacagcaac ataacaaacc gcaaacaaa aggtagaagt aaaaatagca      60
aatagcgcag aataaccgac atcgccctca taaaacgaag gctcaaagct cggctgctga    120
```

-continued

```
ttctcatttc tctcatctcc attcttcttt ctcatcgtat tacctttcc gctctttatc      180 tccaagaaca ataataatct tttcgcctct taatcacaca ggcgaaatga tcccttccac      240
cgccgccgcc ctcctcaccc tcacagctgg tgccgccttc gcccataccg atgtggtgg      300 ccacgagatt ggtcggcgaa atgttggcgg tcccatgttg tatcgtcgag ctgtcaccga     360
tgaagctagt gctgctgtca gtacaggtag gttaatacaa tacaatacaa tcgtattcta     420
tgacaatgac tgaccataac gaccacgtag acatcaacac cgagtgtaca gcctacagtt     480
atgcccctgt gaccgagttg atatcctctt tcccgactat ttggcagact gcttccatcc     540
cctccaatga cacagaagcc caacaacttt tgggaaaat taactccact cttaatacca      600
agattccaaa tgatgtaccc cacggaaccc ccacgggtga ttggaccggt gtgaactact     660
ctaacagtga cccggactgt tggtggactc ataacaagtg cacgactcct tccaacgaca     720
ctggtttgca agccgatatc tccatcgcac ccgagccaat gacatggggt ttgggttttg     780
acgatggacc taactgtagt cacaacgctt tgtatgatct tcttttggag aacaaccaga     840
aggctaccat gtacgtgatc atctctcttt attcatgtcc aaactatgt atgtaaaagg      900 tttttcattg gatccaatgt cttggactgg cctctccagg ctatgagggc tcacgacgaa     960
ggtcatgaaa tatgtgttca cacctggtct catcaataca tgaccgccct cagtaacgag     1020
gtcgtctttg ccgaattgta ctacacccag aaagccatca aggctgttct cggagttact     1080
ccccagtgct ggtatgttgg cactttggtg gaatcgtgtg agactatagc taatgatgac     1140
acaggcgacc tccgtacggt gatgtcgaca acagagttcg tatgattgcc gagggactca     1200
acctgactac catcatctgg tcagacgaca ccgatgactg ggcggctgga accaacggcg     1260
tcactgagca agacgtcaca aataactacc agtcagtgat cgacaaggct ggtaacggta     1320
catacactac tcacggcccc gttgttctta accacgagct cagtaagtct ctcccaacga     1380
ctaaaccgat gtttgctcac gatgtcctct tcagccaact acaccatgtc tgtcttcatg     1440
actatgttcc ccaagatcaa atcagctttc aactacattg tccccatttg cactgcatac     1500
aacatcaccc aaccatatgc cgaaagtaat atcacttgtc ccaactttga aacttacatc     1560
tctggtgtca aaacatcag cagctctacc actcagaaag atggaagcag ctcaacaaac     1620
actgcttctg gttccggcgc cgctggtagt gccagtgcca ctagcagcag cgacgactca     1680
agcagctctg gtggctcaag cggctctagt ggctcaaaca acgctagcag tggtgctttg     1740
ggcatgttcg acagtttgtc aggagtgggt cttattttgg ggggtgtagt tgctggtgtg     1800
atgctgctgt aatgtgatgt gctttagcac gaaaaaaatg gacagtatat caaacgtcac     1860
atgacgtact atgtatccaa acggacaata ttacaatatt attcttaatg catcatacaa     1920
acatagtagc attgccataa tcctgaagtc tactggttcg ggtgagacac ccgtcaatct     1980
aattctgtta agggcatttg atgattgtca gttctacgta gtgccgaaac gaagattgag     2040
tttctgttat ctaacagacg aaaaggaacg ctgatatgca ctgccattta tctgagatcc     2100
aatg                                                                  2104
```

<210> SEQ ID NO 7
<211> LENGTH: 3341
<212> TYPE: DNA
<213> ORGANISM: Cryptococcus neoformans grubii

<400> SEQUENCE: 7

```
ggcatgtcgt gattaattat ttgacatttt gttctattcg tttcagatcc agtaatagtt       60
tttttctctt tatctttgtt gtgtgagttg aaatgaagtg gggggcgtcg acttgggtgt      120
```

```
aattcttcat cgcctgctga acaggttgca ctgttggcaa ggagagcagt tggtgtggat    180
tggataggac ttttttccttg gtctatacga caatcaatag cccgaagata gtagatcaga   240
tgatatgata tatgctgatt atcttcattg ggctagcaca gcacagcgtt agcagacggt    300
agcagtcatg cttttctcac ctcagtccat cggagattga agatcggaga tcctgtgtgc    360
tacatgcatg agctgttgta agggacaaat tgcagaacac tgcaatgaac taactattaa    420
ctaggagctt gaaagtcagg agatcaatga tcaggaagaa aaatcatcgg aattcccatg    480
ctatttgtgt acatataata agatgcacat ttgttctgag cgataatttt gcttttttata   540 tctatccatt taggctaata ccagtactac gtacttcgca tttcacagtt cacagagtag    600
tacatacgta cagataacac agcatcacaa acccagatac caccacagac tgcatcacag    660
tagcaacatg gagtctgagc tttgggagtt gattgagaga cttgttgaat tgcctgtgaa    720
gagccgtata attgactgtc tgaaattata ctgtctttaa tggggactgg agactcatca    780
aataaaactt gactcgcatg ttgaggacca ttgatgccgt gagcatgtgt ttattatgga    840
tatggacgga tactatggct aagtaagaat ctgatgttcc tgttattgcc tctttcatca    900
tcatacagtt cggcgaacct tgtgcaaaga tagccctgag ataagtgtac gacggaaaca    960
tgtccctgag cgacgggtat gaaatattca gggtcttcac aagtcgcaat ccgcaatccg   1020 gcattttttca ccatttgccg tatccggcct cggctccgta cgtattccca ccaagaatct   1080
aacacaacac caacaaacac ctataaactt cactgcttct tcccctcccc ttcttcatca   1140
gcgctgcccc tccatcctct cacctcccct actgcctata ccacgatcct cttccctcac   1200 acataaccctc ctcctctctc tttctcccct atctttttctt cggtacgtct gtttactcac  1260
ccatcaagcg gtttattgtt gtgtacctat gatccttccc aattcgatca aatcagttgg   1320
tgtctaactt cgcacgcagt cttttctgtac aagaagttgc tctcccttc tgtcttttcgg  1380 cataacgtca gcctcttgcc cacccccaca caaccacatg taagcacatc ctctaagcac   1440
atcctctcct ttcgtctaca aacggagaaa ctattacgta tacaacagga caagggctga   1500
ctttaaccta ttcaatcaga acggcccgtt agaatgtacg gtcatttatc tctctccgca   1560 cttttccttgt ttgcagtggt ggccgctgct ccattccggg agtcatggct tcagcctaga   1620
gattcccccg tctcacagct gttcagacga actgctcccg atcccaactc caatggtcag   1680
taccatcttc tactatctct caataagtag gacgagattt cactcatatt cctttataga   1740
ttacatgagt tactatccag gccctgggtc cactccgaac gtcagcacca ttccccaagc    1800
ttggttggat aaacttgcca cagtgaactt gccaaatgtt ccagtagcta cacctgatgg   1860
tggtcgtcct acttacccta ataatgagga cgatggtgac tcgacaattt gttctttcac    1920
cgatcaatgc cgcgtagagg acgatctgta ctctcccccg ggtgagaaga tctgggccgt   1980
gagtgttata tacttctcca ttcattgtca tctagagatg tgattaacgc gggtatacag   2040 cttttccttcg acgatggacc cacagacgtc agtcctgctc tctacgacta tctggctcag   2100
aacaacatat cgtcctctgc gactcatttc atgatcggcg gtaatgttat tacttcgtat    2160
gtctcgacct gcagcatgtc cctgcaggtg ttgtaatatt gactttgtga aatgtaacag    2220
cccacagtca gttctcgttg ccgttaaggc tggaggtcac cttgccgtcc acacttggtc    2280
ccatccttat agtgagtatt tgttaaatta aagcacgatt agtttttaag tcatttcttg    2340
cagtgacaac tcttaccaac gagcaagtcg ttggagagct cggctggacc atgcaggccc    2400
ttagcgatct caatggtggc cgaattccca tgtactggcg ccctccgtat ggagatgttg   2460
acaaccgtgt ccgagctatt gcgaaggaag tatttggctt ggtgactgtc ctttgggatt    2520
```

-continued

| | |
|---|---|
| cgggtgagca tcttgcttca tgctgtggat aaattgctaa tggatcatag acaccaatga | 2580 |
| ttgggctatt accgacgagc caggccagta ctctgttgca agcgttgagg cttacttcga | 2640 |
| cactttggtc actggcaatc gaacccaagg tcttttgctc ttagaacatg agctggataa | 2700 |
| caacactgtt gaagtcttcg aaacggagta ccccaaggca gtgggtaatg gatggactgt | 2760 |
| caagaatgtg gccgatgctt ttaacatgga atggtacctg aactctggca agggcaacaa | 2820 |
| cgacgttgtc acaactatgt ctgttgccgg taccctgacc acggccacgc caactaatac | 2880 |
| ttctacctat gtcgcttcct caactgcagc ctccagtgct tcagtcacgg actcagccgg | 2940 |
| tgtgtcgatt gcctctgctg cgagctccga agcgtcttct tcgtgggcca ttgccaacag | 3000 |
| gccttctcac ttcgtcatcg ccatcgcgtg cggccttgcc cttgctgcta taatggtctg | 3060 |
| atagatgcca tgtgcacttt tttgtcggtc tttttagatc atggactctc attcgcatta | 3120 |
| tataggaatc atggacatat aattcatttt tattgccata gacagtcaag gattgttaga | 3180 |
| ttgtagcagt acattgtttt ttttcttttt ttgtgaataa tggacaattt atttagtagt | 3240 |
| tgtttaatta atcgtcatca acattcatta gctttttcat ttaatagcac aacaaggccg | 3300 |
| gcaaccaaaa tgagtagaac atgtatactg tcttcacaac a | 3341 |